(12) United States Patent
Behrooz

(10) Patent No.: US 10,813,614 B2
(45) Date of Patent: Oct. 27, 2020

(54) SYSTEMS AND METHODS FOR AUTOMATED ANALYSIS OF HETEROTOPIC OSSIFICATION IN 3D IMAGES

(71) Applicant: PerkinElmer Health Sciences, Inc., Waltham, MA (US)

(72) Inventor: Ali Behrooz, Waltham, MA (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 227 days.

(21) Appl. No.: 15/604,350

(22) Filed: May 24, 2017

(65) Prior Publication Data

US 2018/0338740 A1 Nov. 29, 2018

(51) Int. Cl.
| | | |
|---|---|---|
| G06T 7/187 | (2017.01) | |
| A61B 6/00 | (2006.01) | |
| G06T 7/136 | (2017.01) | |
| G06T 7/11 | (2017.01) | |
| G06T 7/13 | (2017.01) | |

(Continued)

(52) U.S. Cl.
CPC .......... A61B 6/5217 (2013.01); A61B 6/032 (2013.01); A61B 6/505 (2013.01); G06F 3/04842 (2013.01); G06K 9/6202 (2013.01); G06T 5/20 (2013.01); G06T 7/0012 (2013.01); G06T 7/11 (2017.01); G06T 7/13 (2017.01); G06T 7/136 (2017.01); G06T 7/187 (2017.01); G06T 2207/10028 (2013.01); G06T 2207/10081 (2013.01); G06T 2207/20012 (2013.01);

(Continued)

(58) Field of Classification Search
CPC ....... A61B 6/5217; A61B 6/032; A61B 6/505; G06T 7/136; G06T 7/0012; G06T 5/20; G06T 7/13; G06T 7/11; G06T 7/187; G06T 2207/30008; G06T 2207/20012; G06T 2207/20152; G06T 2207/10028; G06T 2207/10081; G06K 9/6202; G06F 3/04842
USPC ....................................................... 382/131
See application file for complete search history.

(56) References Cited

U.S. PATENT DOCUMENTS

| 6,625,303 B1 | 9/2003 | Young et al. |
| 7,539,332 B1 | 5/2009 | Al-Dayeh et al. |

(Continued)

FOREIGN PATENT DOCUMENTS

| EP | 2194505 A1 | 6/2010 |
| WO | WO-2009/101560 A2 | 8/2009 |

(Continued)

OTHER PUBLICATIONS

Waarsing, Jan H., Judd S. Day, and Harrie Weinans. "An improved segmentation method for in vivo μCT innaging." Journal of Bone and Mineral Research 19.10 (2004): 1640-1650. (Year: 2004).*

(Continued)

*Primary Examiner* — Amandeep Saini
(74) *Attorney, Agent, or Firm* — Banner & Witcoff, Ltd.

(57) ABSTRACT

Presented herein are systems and methods that facilitate automated segmentation of 3D images of subjects to distinguish between regions of heterotopic ossification (HO) normal skeleton, and soft tissue. In certain embodiments, the methods identify discrete, differentiable regions of a 3D image of subject (e.g., a CT or microCT image) that may then be either manually or automatically classified as either HO or normal skeleton.

25 Claims, 14 Drawing Sheets
(10 of 14 Drawing Sheet(s) Filed in Color)

(51) Int. Cl.

| | |
|---|---|
| A61B 6/03 | (2006.01) |
| G06F 3/0484 | (2013.01) |
| G06K 9/62 | (2006.01) |
| G06T 5/20 | (2006.01) |
| G06T 7/00 | (2017.01) |

(52) U.S. Cl.
 CPC ............... *G06T 2207/20152* (2013.01); *G06T 2207/30008* (2013.01)

(56) References Cited

U.S. PATENT DOCUMENTS

| | | | |
|---|---|---|---|
| 8,306,305 | B2 | 11/2012 | Porat et al. |
| 9,192,348 | B2 | 11/2015 | Ollilainen et al. |
| 2005/0163358 | A1 | 7/2005 | Moeller |
| 2008/0107318 | A1 | 5/2008 | Kiraly |
| 2010/0128954 | A1 | 5/2010 | Ostrovsky-Berman et al. |
| 2012/0143037 | A1 | 6/2012 | Najarian et al. |
| 2013/0163836 | A1* | 6/2013 | Pau ........................... G06T 7/00 382/128 |
| 2016/0038124 | A1 | 2/2016 | Tsujita |
| 2017/0032518 | A1* | 2/2017 | Behrooz ................. G06K 9/52 |
| 2017/0273651 | A1 | 9/2017 | Behrooz et al. |
| 2018/0374209 | A1* | 12/2018 | Patil ...................... G06T 7/0012 |

FOREIGN PATENT DOCUMENTS

| | | | | |
|---|---|---|---|---|
| WO | WO-2014/050601 | A1 | 4/2014 | |
| WO | WO-2017/019059 | A1 | 2/2017 | |
| WO | WO-2017/164893 | A1 | 9/2017 | |
| WO | WO-2018023917 | A1 * | 2/2018 | ............... G06T 7/00 |

OTHER PUBLICATIONS

Zhang, Jing, et al. "Fast segmentation of bone in CT images using 3D adaptive thresholding." Computers in biology and medicine 40.2 (2010): 231-236. (Year: 2010).*
Analyzedirect, Analyze 12.0 Bone Microarchitecture Analysis Manual, AnalyzeDirect, Inc. and BIR, Mayo Clinic, 56 pages, 1999-2014.
Ballard, Dana H., Model-Directed Detection of Ribs in Chest Radiographs, Computer Science Department, University of Rochester, (1978) 24 pages.
Computer Vision Demonstration Website, Electronics and Computer Science University of Southampton, Standard and Hysteresis Thresholding, 2 pages (2005) [retrieved May 3, 2017—<http://users.ecs.saoton.ac.uk/msn/book/new_demo/thresholding/>].
De Bruijne, M. and Nielsen, Multi-object Segmentation Using Shape Particles, IPMI, LNCS 3565:762-773 (2005).
Eddins, Steve, The Watershed Transform: Strategies for Image Segmentation, MathWorks, 8 pages (2002) [retrieved May 3, 2017—<https://www.mathworks.com/company/newsletters/articles/the-watershed-transform-strategies-for-image-segmentation.html>].
Fiebich, M. et al., Automatic Bone Segmentation Technique for CT Angiographic Studies, Journal of Computer Assisted Tomography, 23(1):155-161 (1999).
Frangi, A. F. et al., Mutliscale vessel enhancement filtering, Medical Image Computing and Computer-Assisted Intervention, Lecture Notes in Computer Science, 1496:130-137 (1998).
Khmelinskii, A. et al., Atlas-based organ & bone approximation for ex-vivo 1/4 MRI mouse data: A pilot study, IEEE ISBI, 1197-1200 (2010).
Klinder, T. et al., Automated Model-Based Rib Cage Segmentation and Labeling in CT Images, MICCA, Part II, LNCS 4792:195-202 (2007).
Krčah, M. et al., Fully Automatic and Fast Segmentation of the Femur Bone From 3D-CT Images With No Shape Prior, IEEE, pp. 2087-2090, ISBI2011.
Laib, A. et al., 3D Micro-Computed Tomography of Trabecular and Cortical Bone Architecture with Application to a Rat Model of Immobilisation Osteoporosis, Medical and Biological Engineering and Computing, 38(3):326-332 (2000).
Lee, J. and Reeves, A. P., Segmentation of Individual Ribs from Low-dose Chest CT, Medical Imaging, 7624:J1-J8 (2010).
Lee, T.C. et al., Building Skeleton Models Via 3-D Medial Surfaces/Axis Thinning Algorithms, CVGIP: Graphical Models and Image Processing, Academic Press, 56(6):462-478 (1994).
Lemke, H. et al., CAR '97, Computer Assisted Radiology and Surgery, Elsevier, 209-214 (1997).
Maier, F. et al., Automatic Liver Segmentation Using the Random Walker Algorithm, Universität Karlsruhe (TH), Siemens Medical Solutions, Forchheim, Friedrich-Alexander University, Erlangen-Nuremberg, RWTH Aachen University, 6 pages (2008).
Mavrogenis, A. F. et al., Heterotopic Ossification Revisited, Orthopedics, 34:(3)177 (2011).
Meyer, F. and Beucher, S., Morphological Segmentation, Journal of Visual Communication and Image Representation, 1(1):21-46 (1990).
Otsu, Nobuyuki, A Threshold Selection Method from Gray-Level Histograms, IEE Transactions on Systems, Man and Cybernetics, SMC-9(1):62-66 (1979).
Smolka, Jakub, Watershed based region growing algorithm, Annales UMCS Informatica AI, 3:169-178 (2005).
Staal, J. et al, Automatic rib segmentation and labeling in computed tomography scans using a general framework for detection, recognition and segmentation of objects in volumetric data, Medical Image Analysis 11:35-46 (2007).
Staal, J. et al., Automatic Rib Segmentation in CT Data, CVAMIA-MMBIA, LNCS 3117:193-204 (2004).
Sun, S. et al., Automated 3-D Segmentation of Lungs With Lung Cancer in CT Data Using a Novel Robust Active Shape Model Approach, IEEE Transactions on Medical Imaging, 31(2):449-460 (2012).
Waarsing, J. H. et al., An Improved Segmentation Method for in Vivo μCT Imaging, Journal of Bone and Mineral Research, 19:1640-1650 (2004).
Wang, H. et al., Estimation of Mouse Organ OLocations Through Registration of a Statistical Mouse Atlas With Micro-CT Images, IEEE Transactions on Medical Imaging, 31(1):88-102 (2012).
Wikipedia, Canny edge detector, 9 pages (2017) [retrieved May 3, 2017—<https://en.wikipedia.org/wiki/Canny_edge_detector>].
Wildeman, M. H. et al., 2D/3D Registration of Micro-CT Data to Multi-View Photographs Based on a 3D Distance Map, Biomedical Imaging, IEEE International Symposium ON, 987-990 (2009).
Wlodarczyk, J. et al., Segmentation of bones in magentic resonance images of the wrist, International Journal of Computer Assisted Radiology and Surgery, 10(4):419-431 (2014).
Wu, D. et al, A Learning Based Deformable Template Matching Method for Automatic Rib Centerline Extraction and Labeling in CT Images, IEEE, 980-987 (2012).
Yin, Y. et al., Hierarchical Decision Framework with Priori Shape Models for Knee Joint Cartilage Segmentation—MICCAI Grand Challenge, Depts. of Electrical & Computer Engineering and Orthopaedics & Rehabilitation, University of Iowa, pp. 241-250 (2010).
Li, Q. et al., Selective enhancement filters for nodules, vessels, and airway walls in two- and three-dimensional CT scans, Med. Phys. 30(8):2040-2051 (2003).
Sato, Y. et al., 3D Multi-Scale Line Filter for Segmentation and Visualization of Curvilinear Structures in Medical Images, Medical Image Analysis 2(2):143-168 (1998).
Zhang et al. "Fast segmentation of bone in CT images using 3D adaptive thresholding". Computers in Biology and Medicine, New York, NY, US, vol. 40, No. 2. Feb. 1, 2010, pp. 231-236.
Nysjo et al. "Precise 3D Angle Measurements in CT Wrist Images". ICIAP 2013, Part II, LCNCS 8157, pp. 479-488, 2013.
Yabo Fu et al. "Automatic and hierarchical segmentation of the human skeleton in CT images". IOP, Physics in Medicine and Biology, vol. 62, No. 7, Mar. 14, 2017, pp. 2812-2833.
Kim, Cheol-Hwan et al. "Medical Image Segmentation by Improved 3D Adaptive Thresholding". ICTC 2015, IEEE, Oct. 28, 2015, pp. 263-265.

(56) References Cited

OTHER PUBLICATIONS

Behrooz, A. et al., Automated Quantitative Bone Analysis in In Vivo X-ray Micro-Computed Tomography, IEEE Transactions on Medical Imagining, 36(9):1955-1965 (2017).

Beucher, S. and Meyer, F., The Morphological Approach to Segmentation: The Watershed Transformation, Mathematical Morphology in Image Processing, Marcel Dekker, New York, Chapter 12, pp. 433-481 (1992).

* cited by examiner

SYSTEMS AND METHODS FOR AUTOMATED ANALYSIS OF HETEROTOPIC OSSIFICATION IN 3D IMAGES

FIELD OF THE INVENTION

This invention relates generally to methods and systems of image processing and analysis. More particularly, in certain embodiments, the invention relates to automatic splitting and segmentation of heterotopic ossification from an anatomical image of a small subject (e.g., small animal, small mammal), e.g., captured with a computed tomography (CT) scanner.

BACKGROUND OF THE INVENTION

There is a wide array of technologies directed to in vivo imaging of mammals—for example, bioluminescence, fluorescence, tomography, and multimodal imaging technologies. In vivo imaging of small mammals is performed by a large community of investigators in various fields, e.g., oncology, infectious disease, and drug discovery.

In vivo micro computed tomography (hereafter, "microCT") imaging, is an x-ray-based technology that can image tissues, organs, and non-organic structures with high resolution, although higher-throughput imaging may make beneficial use of lower resolution microCT imaging to speed image acquisition and/or processing while maintaining acceptable accuracy and image detail. MicroCT has evolved quickly, requiring low dose scanning and fast imaging protocols to facilitate multi-modal applications and enable longitudinal experimental models. In vivo imaging often involves the use of reagents, such as fluorescent probes, for non-invasive spatiotemporal visualization of biological phenomena inside a live animal. Multi-modal imaging involves the fusion of images obtained in different ways, for example, by combining FMT, PET, MRI, CT, and/or SPECT imaging data.

Image analysis applications and/or imaging systems generally allow for visualization, analysis, processing, segmentation, registration and measurement of biomedical images. These applications and systems also provide volume rendering tools (e.g., volumetric compositing, depth shading, gradient shading, maximum intensity projection, summed voxel projection, signal projection); manipulation functions (e.g., to define areas of structures of interest, delete unwanted objects, edit images and object maps); and measurement functions (e.g., for calculation of number of surface voxels, number of exposed faces, planar area of a region, and estimated surface area or volume of a region).

Image segmentation techniques are often used to identify separate regions of images that correspond to different structures, organs, and/or tissue of interest. Where different structures of interest are similar in nature and/or found in close proximity to each other, accurate and robust image segmentation can be challenging. For example, segmentation of representations of individual bones (e.g., to differentiate between individual bones) is a challenge that a number of image segmentation techniques have been developed to address.

These segmentation challenges are also encountered in the analysis of images of certain diseases. For example, certain diseases produce structural features such as abnormal growths of tissue. Identification and analysis of such features can provide valuable insight regarding disease state and progression in a subject, as well as the efficacy of various treatments. Such abnormal growths are comprised of tissue that is also found in normal, healthy subjects, yet for analysis purposes must be separated and differentiated from normal structures of the same tissue. This makes image analysis of such diseases more complicated.

One such disease is heterotopic ossification (HO), also referred to as ectopic bone or extra-skeletal bone formation. HO is a disease in which bone forms in soft connective tissue outside of normal skeleton. HO may result from trauma or surgery, e.g., joint replacement surgery, or it may be caused by rare genetic disorders such as fibrodysplasia ossificans progressiva (FOP) or progressive osseous heteroplasia (POH). Mouse models of HO are frequently used in the study of HO, to, for example, provide knowledge into identification of the causes of HO (e.g., genetic, trauma, etc.) and mechanisms that regulate abnormal bone formation. Study of HO in mouse models also provides insight into treatment approaches. MicroCT imaging is often used in the study of HO formation and progression in vivo, as microCT images provide sufficient contrast between HO and soft tissue. An example of a microCT scan of the hind limbs of a mouse model with late-stage HO is shown in FIG. 1. The extra-skeletal ossified masses corresponding to HO are manually-identified in the figure, and are located adjacent and running parallel to the tibia bones of the mouse model. Analysis and quantification of heterotopic ossification formation and structural features can provide insight useful for developing understanding of disease diagnosis, state, and progression in a subject, as well as analysis of efficacy and kinetics of different treatments. However, heretofore, identification of HO regions has been performed manually.

Accordingly, there exists a need for improved systems and methods for automated detection and segmentation of related structural features within a subject. In particular, there exists a need for systems and methods that can automatically differentiate between normal, healthy structures and abnormal growths that are of the same or similar tissue types. Such approaches are particularly relevant to the study of diseases such as HO.

SUMMARY OF THE INVENTION

Presented herein are systems and methods that facilitate automated segmentation of 3D images of subjects to distinguish between regions of heterotopic ossification (HO), normal skeleton, and soft tissue. In certain embodiments, the methods identify discrete, differentiable regions of a 3D image of subject (e.g., a CT or microCT image) that may then be either manually or automatically classified as either HO or normal skeleton.

The approaches described herein utilize a hybrid thresholding approach as well as multiple splitting operations. In certain embodiments, the hybrid thresholding approach and multiple splitting operations account for unique image processing challenges posed by the physical characteristics of HO and resulting characteristics of image regions representing HO. The approaches described herein thereby provide for detection and segmentation of regions in an image corresponding to normal skeleton and HO in a robust and computationally efficient fashion. The detection and segmentation approaches described herein thereby facilitate streamlined quantitative analysis of HO formation, including analysis of morphometric attributes, density, and structural parameters. For example, automated quantification of HO volume in longitudinal studies provides insight into efficacy and kinetics of different treatments. Accordingly, by allowing improved quantitative analysis of HO in this manner, the systems and methods described herein provide a valuable tool for assessing disease state and/or progression in a subject and for assessing treatment efficacy.

In one aspect, the invention is directed to a method for automatically detecting heterotopic ossification (HO) in a 3D image of a subject (e.g., an anatomical image of the subject), the method comprising: (a) receiving, by a processor of a computing device, a 3D image of a subject [e.g., wherein the image is an anatomical image (e.g., a CT image, e.g., a microCT image)]; (b) applying, by the processor, a global thresholding operation to the received 3D image to produce an initial bone mask that identifies an initial region of interest within the image comprising a graphical representation of bone (e.g., including normal skeleton and HO) [e.g., wherein the initial bone mask is a binary mask comprising a plurality of voxels, each initial bone mask voxel corresponding to a voxel of the received 3D image, wherein initial bone mask voxels identified as corresponding to bone (e.g., including normal skeleton and HO, as initially assessed by the global thresholding operation) are assigned a first value (e.g., a numeric 1; e.g., a Boolean 'true') and voxels identified as corresponding to non-bone tissue are assigned a second value (e.g., a numeric 0; e.g., a Boolean 'false')]; (c) determining, by the processor, a boundary value map using a 3D edge detection operation applied to the initial region of interest of the image identified by the initial bone mask, wherein the boundary value map identifies and includes intensity values of voxels of the 3D image that correspond to boundaries where bone meets soft tissue [e.g., wherein the boundary value map comprises a plurality of voxels, each corresponding to a voxel of the 3D image within the region of interest, and wherein boundary value map voxels identified as corresponding to boundaries where bone meets soft tissue are assigned an intensity value of the corresponding voxel of the 3D image and all other boundary value map voxels are assigned a null value (e.g., a numeric 0)]; (d) determining, by the processor, a bone threshold map using the initial bone mask and the boundary value map, wherein the bone threshold map comprises, for each voxel of the initial bone mask, a threshold value determined by extrapolating values of the boundary value map to voxels within the initial bone mask [e.g., wherein the bone threshold map comprises a plurality of voxels, each corresponding to a voxel within the initial region of interest identified by the initial bone mask, wherein each bone threshold map voxel is assigned the determined threshold value for that voxel]; and (e) determining, by the processor, a final bone mask (e.g., including normal skeleton and HO) using the bone threshold map and the received 3D image [e.g., by identifying voxels of the initial region of interest with intensities above a value of a corresponding voxel of the bone threshold map as corresponding to bone (e.g., including normal skeleton and HO); e.g., wherein the bone and HO mask comprises a plurality of voxels, each corresponding to a voxel of the 3D image within the initial region of interest, wherein, for each voxel of the 3D image, the corresponding voxel of the final bone mask is identified as bone and assigned a first value (e.g., a numeric 1; e.g., a Boolean 'true') if the 3D image voxel's intensity is above the local threshold value of the corresponding bone threshold map voxel and all other voxels are assigned a second value (e.g., a numeric 0; e.g., a Boolean 'false')].

In certain embodiments, step (b) comprises determining, by the processor, a global threshold value using intensities of voxels of the 3D image [e.g., using a histogram representing a distribution of intensities of voxels of the 3D image].

In certain embodiments, the global threshold value is determined such that the initial bone mask that over represents bone within the 3D image (e.g., the initial bone mask identifies all portions of the 3D image encompassing normal skeleton and HO, said portions also encompassing some non-bone tissue (e.g., soft-tissue) in the 3D image (e.g., the initial bone mask is overly-inclusive to insure all bone and HO is identified)).

In certain embodiments, the global thresholding operation is a hysteresis thresholding operation that uses an upper threshold and a lower threshold determined using the global threshold value (e.g., the upper threshold value is a first fraction of the global threshold value and the lower threshold value is a second fraction of the global threshold value).

In certain embodiments, the method further comprises: (f) determining, by the processor, a distance map by applying a distance transform to the final bone mask [e.g., wherein the distance map comprises a plurality of distance map voxels, each of which corresponds to a voxel of the final bone mask and has (e.g., is assigned) a distance value that represents a distance from the voxel to a nearest boundary and/or non-bone voxel (e.g., a voxel of the final bone mask having a value of 0)]; (g) applying, by the processor, a watershed segmentation operation to the distance map to identify a set of catchment basins and/or watershed lines within the distance map [e.g., such that the distance map is partitioned into a plurality of catchment basins that are separated from each other by watershed lines; e.g., wherein the watershed segmentation operation produces a watershed mask comprising a plurality of catchment basins (e.g., each catchment basin corresponding to a connected region of voxels assigned a first value such as a numeric 1 or Boolean 'true') separated from each other by watershed lines (e.g., each watershed line corresponding to a connected line of voxels assigned a second value, such as a numeric 0 or Boolean 'true')]; (h) generating, by the processor, a first split bone mask using the final bone mask and the identified catchment basins and/or watershed lines from step (g) [e.g., by removing voxels corresponding to watershed lines from the final bone mask, thereby generating the first split bone mask; e.g., by masking the watershed mask with the final bone mask (e.g., by performing a logical voxel-by-voxel AND operation between the watershed mask and the final bone mask), thereby generating the first split bone mask]; (i) applying, by the processor, one or more second derivative splitting filters to the 3D image to identify a set of split line voxels within the 3D image; (j) removing, by the processor, voxels corresponding to the set of split line voxels from the first split bone mask [e.g., by setting their value to the second value, which identifies soft tissue (e.g., a numeric 0; e.g., a Boolean 'false')], thereby generating the second split bone mask; (k) determining, by the processor, a plurality of labeled split binary components of the second split bone mask via one or more morphological processing operations (e.g., connected component labeling and/or by identifying catchment basins using distance and watershed transforms); (l) performing, by the processor, a region growing operation within the final bone mask using the plurality of labeled spit binary components of the second split bone mask as seeds, thereby producing a labeled final bone map (e.g., the labeled final bone map comprising a plurality of labeled regions, the entirety of each region corresponding to either normal skeleton or HO); and (m) rendering, by the processor, a graphical representation of the labeled final bone map (e.g., for display to a user, e.g., wherein the graphical representation visually distinguishes differently labeled regions of the labeled final bone map, e.g., using different colors).

In certain embodiments, the method further comprises: (f) applying, by the processor, one or more second derivative splitting filters to the 3D image to identify a set of split line voxels within the 3D image; (g) removing, by the processor, voxels corresponding to the set of split line voxels from the final bone mask [e.g., by setting their value to the second value, which identifies soft tissue (e.g., a numeric 0; e.g., a Boolean 'false')], thereby generating a first split bone mask; (h) determining, by the processor, a distance map by applying a distance transform to the first split bone mask [e.g., wherein the distance map comprises a plurality of distance map voxels, each of which corresponds to a voxel of the first split bone mask and has (e.g., is assigned) a distance value that represents a distance from the voxel to a nearest boundary and/or non-bone voxel (e.g., a voxel of the first split bone mask having a value of 0)]; (i) applying, by the processor, a watershed segmentation operation to the distance map to identify a set of catchment basins and/or watershed lines within the distance map [e.g., such that the distance map is partitioned into a plurality of catchment basins that are separated from each other by watershed lines; e.g., wherein the watershed segmentation operation produces a watershed mask comprising a plurality of catchment basins (e.g., each catchment basin corresponding to a connected region of voxels assigned a first value such as a numeric 1 or Boolean 'true') separated from each other by watershed lines (e.g., each watershed line corresponding to a connected line of voxels assigned a second value, such as a numeric 0 or Boolean 'true')]; (j) generating, by the processor, a second split bone mask using (A) the first split bone mask and (B) the identified catchment basins and/or watershed lines from step (i) [e.g., by removing voxels corresponding to watershed lines from the first split bone mask, thereby generating the second split bone mask; e.g., by masking the watershed mask with the first split bone mask (e.g., by performing a logical voxel-by-voxel AND operation between the watershed mask and the first split bone mask), thereby generating the second split bone mask]; (k) determining, by the processor, a plurality of labeled split binary components of the second split bone mask via one or more morphological processing operations (e.g., connected component labeling and/or by identifying catchment basins using distance and watershed transforms); (l) performing, by the processor, a region growing operation within the final bone mask using the plurality of labeled spit binary components of the second split bone mask as seeds, thereby producing a labeled final bone map (e.g., the labeled final bone map comprising a plurality of labeled regions, the entirety of each region corresponding to either normal skeleton or HO); and (m) rendering, by the processor, a graphical representation of the labeled final bone map (e.g., for display to a user, e.g., wherein the graphical representation visually distinguishes differently labeled regions of the labeled final bone map, e.g., using different colors).

In certain embodiments, the method comprises: (n) following step (m), receiving, by the processor, via a graphical user interface (GUI), a user selection of one or more of a plurality of labeled regions of the labeled final bone map, wherein the user selection corresponds to an identification of the one or more labeled regions as corresponding to HO; and (o) labeling, by the processor, the one or more labeled regions selected by the user as corresponding to HO and labeling, by the processor, the remaining labeled regions as corresponding to normal skeleton, thereby producing a binary labeled normal skeleton and HO map that differentiates between regions of the 3D image corresponding to normal skeleton and regions of the image corresponding to HO.

In certain embodiments, the method comprises determining, by the processor, one or more morphometric measurements (e.g., for diagnostic purposes; e.g., for determining treatment efficacy) using the binary labeled normal skeleton and HO map.

In certain embodiments, the method comprises determining, by the processor, a total volume of the regions of the binary labeled normal skeleton and HO map that are labeled as corresponding to HO.

In certain embodiments, the one or more second derivative splitting filters comprises at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

In certain embodiments, applying the one or more second derivative splitting filters comprises applying a plurality of second derivative splitting filters, wherein applying the plurality of second derivative splitting filters comprises: for each second derivative splitting filter being applied, producing a filtered image and identifying voxels of the filtered image with intensity higher or lower than a threshold value (e.g., a predetermined threshold value) as split line voxels.

In certain embodiments, the method comprises: prior to applying the one or more second derivative splitting filters, performing, by the processor, a Gaussian filtering operation on the 3D image to produce a Gaussian filtered version of the 3D image; and applying, by the processor, the one or more second derivative splitting filters to the Gaussian filtered version of the 3D image.

In certain embodiments, the 3D image of the subject is a CT image (e.g., a microCT image) and wherein the method comprises acquiring the CT image (e.g., the microCT image).

In another aspect, the invention is directed to a system for automated detection of heterotopic ossification (HO) in a 3D image of a subject (e.g., an anatomical image of the subject), the system comprising: a processor; and a memory having instructions stored thereon, wherein the instructions, when executed by the processor, cause the processor to: (a) receive a 3D image of a subject [e.g., wherein the image is an anatomical image (e.g., a CT image, e.g., a microCT image)]; (b) apply a global thresholding operation to the received 3D image to produce an initial bone mask that identifies an initial region of interest within the image comprising a graphical representation of bone (e.g., including normal skeleton and HO) [e.g., wherein the initial bone mask is a binary mask comprising a plurality of voxels, each initial bone mask voxel corresponding to a voxel of the received 3D image, wherein initial bone mask voxels identified as corresponding to bone (e.g., including normal skeleton and HO, as initially assessed by the global thresholding operation) are assigned a first value (e.g., a numeric 1; e.g., a Boolean 'true') and voxels identified as corresponding to non-bone tissue are assigned a second value (e.g., a numeric 0; e.g., a Boolean 'false')]; (c) determine a boundary value map using a 3D edge detection operation applied to the initial region of interest of the image identified by the initial bone mask, wherein the boundary value map identifies and includes intensity values of voxels of the 3D image that correspond to boundaries where bone meets soft tissue [e.g., wherein the boundary value map comprises a plurality of voxels, each corresponding to a voxel of the 3D image within the region of interest, and wherein boundary value map voxels identified as corresponding to boundaries where bone meets soft tissue are assigned an intensity value of the corresponding voxel of the 3D image and all other boundary value map voxels are assigned a null value (e.g., a numeric 0)]; (d) determine a bone threshold map using the initial bone mask and the boundary value map, wherein the bone threshold map comprises, for each voxel of the initial bone mask, a threshold value determined by extrapolating values of the boundary value map to voxels within the initial bone mask [e.g., wherein the bone threshold map comprises a plurality of voxels, each corresponding to a voxel within the initial region of interest identified by the initial bone mask, wherein each bone threshold map voxel is assigned the determined threshold value for that voxel]; and (e) determine a final bone mask (e.g., including normal skeleton and HO) using the bone threshold map and the received 3D image [e.g., by identifying voxels of the initial region of interest with intensities above a value of a corresponding voxel of the bone threshold map as corresponding to bone (e.g., including normal skeleton and HO); e.g., wherein the bone and HO mask comprises a plurality of voxels, each corresponding to a voxel of the 3D image within the initial region of interest, wherein, for each voxel of the 3D image, the corresponding voxel of the final bone mask is identified as bone and assigned a first value (e.g., a numeric 1; e.g., a Boolean 'true') if the 3D image voxel's intensity is above the local threshold value of the corresponding bone threshold map voxel and all other voxels are assigned a second value (e.g., a numeric 0; e.g., a Boolean 'false')].

In certain embodiments, at step (b), the instructions cause the processor to determine a global threshold value using intensities of voxels of the 3D image [e.g., using a histogram representing a distribution of intensities of voxels of the 3D image].

In certain embodiments, the instructions cause the processor to determine the global threshold such that the initial bone mask that over represents bone within the 3D image (e.g., the initial bone mask identifies all portions of the 3D image encompassing normal skeleton and HO, said portions also encompassing some non-bone tissue (e.g., soft-tissue) in the 3D image (e.g., the initial bone mask is overly-inclusive to insure all bone and HO is identified)).

In certain embodiments, the global thresholding operation is a hysteresis thresholding operation that uses an upper threshold and a lower threshold determined using the global threshold value (e.g., the upper threshold value is a first fraction of the global threshold value and the lower threshold value is a second fraction of the global threshold value).

In certain embodiments, the instructions cause the processor to: (f determine a distance map by applying a distance transform to the final bone mask [e.g., wherein the distance map comprises a plurality of distance map voxels, each of which corresponds to a voxel of the final bone mask and has (e.g., is assigned) a distance value that represents a distance from the voxel to a nearest boundary and/or non-bone voxel (e.g., a voxel of the final bone mask having a value of 0)]; (g) apply a watershed segmentation operation to the distance map to identify a set of catchment basins and/or watershed lines within the distance map [e.g., such that the distance map is partitioned into a plurality of catchment basins that are separated from each other by watershed lines; e.g., wherein the watershed segmentation operation produces a watershed mask comprising a plurality of catchment basins (e.g., each catchment basin corresponding to a connected region of voxels assigned a first value such as a numeric 1 or Boolean 'true') separated from each other by watershed lines (e.g., each watershed line corresponding to a connected line of voxels assigned a second value, such as a numeric 0 or Boolean 'true')]; (h) generate a first split bone mask using the final bone mask and the identified catchment basins and/or watershed lines from step (g) [e.g., by removing voxels corresponding to watershed lines from the final bone mask, thereby generating the first split bone mask; e.g., by masking the watershed mask with the final bone mask (e.g., by performing a logical voxel-by-voxel AND operation between the watershed mask and the final bone mask), thereby generating the first split bone mask]; (i) apply one or more second derivative splitting filters to the 3D image to identify a set of split line voxels within the 3D image; (j) remove voxels corresponding to the set of split line voxels from the first split bone mask [e.g., by setting their value to the second value, which identifies soft tissue (e.g., a numeric 0; e.g., a Boolean 'false')], thereby generating the second split bone mask; (k) determine a plurality of labeled split binary components of the second split bone mask via one or more morphological processing operations (e.g., connected component labeling and/or by identifying catchment basins using distance and watershed transforms); (l) perform a region growing operation within the final bone mask using the plurality of labeled spit binary components of the second split bone mask as seeds, thereby producing a labeled final bone map (e.g., the labeled final bone map comprising a plurality of labeled regions, the entirety of each region corresponding to either normal skeleton or HO); and (m) render a graphical representation of the labeled final bone map (e.g., for display to a user, e.g., wherein the graphical representation visually distinguishes differently labeled regions of the labeled final bone map, e.g., using different colors).

In certain embodiments, the instructions cause the processor to: (f) apply one or more second derivative splitting filters to the 3D image to identify a set of split line voxels within the 3D image; (g) remove voxels corresponding to the set of split line voxels from the final bone mask [e.g., by setting their value to the second value, which identifies soft tissue (e.g., a numeric 0; e.g., a Boolean 'false')], thereby generating a first split bone mask; (h) determine a distance map by applying a distance transform to the first split bone mask [e.g., wherein the distance map comprises a plurality of distance map voxels, each of which corresponds to a voxel of the first split bone mask and has (e.g., is assigned) a distance value that represents a distance from the voxel to a nearest boundary and/or non-bone voxel (e.g., a voxel of the first split bone mask having a value of 0)]; (i) apply a watershed segmentation operation to the distance map to identify a set of catchment basins and/or watershed lines within the distance map [e.g., such that the distance map is partitioned into a plurality of catchment basins that are separated from each other by watershed lines; e.g., wherein the watershed segmentation operation produces a watershed mask comprising a plurality of catchment basins (e.g., each catchment basin corresponding to a connected region of voxels assigned a first value such as a numeric 1 or Boolean 'true') separated from each other by watershed lines (e.g., each watershed line corresponding to a connected line of voxels assigned a second value, such as a numeric 0 or Boolean 'true')]; (j) generate a second split bone mask using (A) the first split bone mask and (B) the identified catchment basins and/or watershed lines from step (i) [e.g., by removing voxels corresponding to watershed lines from the first split bone mask, thereby generating the second split bone mask; e.g., by masking the watershed mask with the first split bone mask (e.g., by performing a logical voxel-by-voxel AND operation between the watershed mask and the first split bone mask), thereby generating the second split bone mask]; (k) determine a plurality of labeled split binary components of the second split bone mask via one or more morphological processing operations (e.g., connected component labeling and/or by identifying catchment basins using distance and watershed transforms); (l) perform a region growing operation within the final bone mask using the plurality of labeled spit binary components of the second split bone mask as seeds, thereby producing a labeled final bone map (e.g., the labeled final bone map comprising a plurality of labeled regions, the entirety of each region corresponding to either normal skeleton or HO); and (m) render a graphical representation of the labeled final bone map (e.g., for display to a user, e.g., wherein the graphical representation visually distinguishes differently labeled regions of the labeled final bone map, e.g., using different colors).

In certain embodiments, the instructions cause the processor to: (n) following step (m), receive, via a graphical user interface (GUI), a user selection of one or more of a plurality of labeled regions of the labeled final bone map, wherein the user selection corresponds to an identification of the one or more labeled regions as corresponding to HO; and (o) label the one or more labeled regions selected by the user as corresponding to HO and label the remaining labeled regions as corresponding to normal skeleton, thereby producing a binary labeled normal skeleton and HO map that differentiates between regions of the 3D image corresponding to normal skeleton and regions of the image corresponding to HO.

In certain embodiments, the instructions cause the processor to determine one or more morphometric measurements (e.g., for diagnostic purposes; e.g., for determining treatment efficacy) using the binary labeled normal skeleton and HO map.

In certain embodiments, the instructions cause the processor to determine a total volume of the regions of the binary labeled normal skeleton and HO map that are labeled as corresponding to HO.

In certain embodiments, the one or more second derivative splitting filters comprises at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

In certain embodiments, applying the one or more second derivative splitting filters comprises applying a plurality of second derivative splitting filters, wherein applying the plurality of second derivative splitting filters comprises: for each second derivative splitting filter being applied, producing a filtered image and identifying voxels of the filtered image with intensity higher or lower than a threshold value (e.g., a predetermined threshold value) as split line voxels.

In certain embodiments, the instructions cause the processor to: prior to applying the one or more second derivative splitting filters, perform a Gaussian filtering operation on the 3D image to produce a Gaussian filtered version of the 3D image; and apply the one or more second derivative splitting filters to the Gaussian filtered version of the 3D image. In certain embodiments, the 3D image of the subject is a CT image (e.g., a microCT image).

In certain embodiments, the system comprises a CT scanner (e.g., a microCT scanner) for acquiring the 3D image of the subject and wherein the instructions cause the processor to acquire the 3D image of the subject using the CT scanner.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

Figure 1:
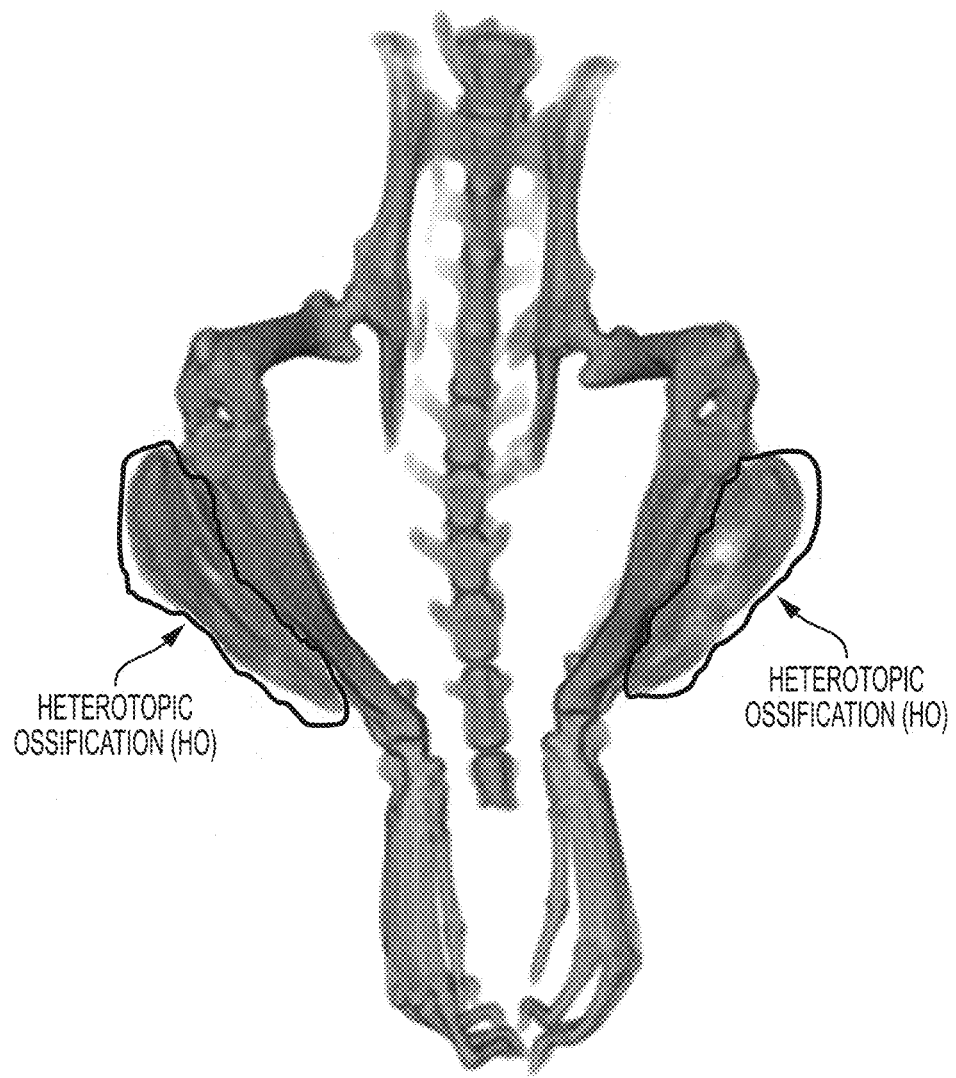
FIG. 1 is a gray scale microCT image of hind limbs of a mouse illustrating normal skeleton and heterotopic ossification (HO).

The patent or application file contains at least one drawing executed in color. Copies of this patent or patent application publication with color drawing(s) will be provided by the Office upon request and payment of the necessary fee.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Image: As used herein, the term "image", for example, as in a three-dimensional image of a mammal, includes any visual representation, such as a photo, a video frame, streaming video, as well as any electronic, digital, or mathematical analogue of a photo, video frame, or streaming video. Any apparatus described herein, in certain embodiments, includes a display for displaying an image or any other result produced by a processor. Any method described herein, in certain embodiments, includes a step of displaying an image or any other result produced by the method.

3D, three-dimensional: As used herein, "3D" or "three-dimensional" with reference to an "image" means conveying information about three spatial dimensions. A 3D image may be rendered as a dataset in three dimensions and/or may be displayed as a set of two-dimensional representations, or as a three-dimensional representation. In certain embodiments, a 3-D image is represented as voxel (e.g., volumetric pixel) data.

Various medical imaging devices and other 3-D imaging devices (e.g., a computed tomography scanner (CT scanner), a microCT scanner, etc.) output 3-D images comprising voxels or otherwise have their output converted to 3-D images comprising voxels for analysis. In certain embodiments, a voxel corresponds to a unique coordinate in a 3-D image (e.g., a 3-D array). In certain embodiments, each voxel exists in either a filled or an unfilled state (e.g., binary ON or OFF).

Mask: As used herein, a "mask" is a graphical pattern that identifies a 2D or 3D region and is used to control the elimination or retention of portions of an image or other graphical pattern. In certain embodiments, a mask is represented as a binary 2-D or 3-D image, wherein each pixel of a 2-D image or each voxel of a 3-D image is assigned one of two values of a binary set of values (e.g. each pixel or voxel may be assigned a 1 or a 0, e.g. each pixel or voxel may be assigned a Boolean "true" or "false" value).

Second derivative splitting filter: As used herein, applying a "second derivative splitting filter" is an image processing operation based on the second derivatives (or approximations thereof) of the intensity of a 3D image, e.g., a grayscale 3D image, at each of a plurality of voxels. In some embodiments, a splitting filter is derived from Gaussian second derivative filters selected from Laplacian of Gaussian (LoG), highest Hessian eigenvalue with preliminary Gaussian filtering (HEH), and lowest Hessian eigenvalue with preliminary Gaussian filtering (LEH).

Split-line voxels: As used herein, the terms "split-line voxels" refer to voxels of a given image and/or mask that are identified and used to remove voxels from a particular mask, thereby splitting the particular mask.

Seed: As used herein, the term "seed" refers to a set of voxels (e.g., a connected set of voxels) that is used as an initial starting region for a growing operation that expands the size of the seed until a particular stop criteria is met. In certain embodiments, the growing operation expands the size of the seed by repeatedly adding to it neighboring voxels.

Label: As used herein, the term "label" refers to an identifier (e.g., a computer representation of an identifier, such as a textual value, a numeric value, a Boolean value, and the like) that is linked to a specific region of an image.

Subject: As used herein, the term "subject" refers to an individual that is imaged. In certain embodiments, the subject is a human. In certain embodiments, the subject is a small animal.

Small animal: As used herein, a "small animal" refers to small mammals that can be imaged with a microCT and/or micro-MR imager. In some embodiments, "small animal" refers to mice, rats, voles, rabbits, hamsters, and similarly-sized animals.

Bone, bone tissue: As used herein, the terms "bone" and "bone tissue" refer to any osseous tissue, and include both normal skeleton and heterotopic ossification (HO).

Link: As used herein, the terms "link", and "linked", as in a first data structure or data element is linked to a second data structure or data element, refer to a computer representation of an association between two data structures or data elements that is stored electronically (e.g. in computer memory).

Provide: As used herein, the term "provide", as in "providing data", refers to a process for passing data in between different software applications, modules, systems, and/or databases. In certain embodiments, providing data comprises the execution of instructions by a process to transfer data in between software applications, or in between different modules of the same software application. In certain embodiments a software application may provide data to another application in the form of a file. In certain embodiments an application may provide data to another application on the same processor. In certain embodiments standard protocols may be used to provide data to applications on different resources. In certain embodiments a module in a software application may provide data to another module by passing arguments to that module.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader— the presence and/or placement of a header is not intended to limit the scope of the subject matter described herein.

Described herein are systems and methods for detection and segmentation of graphical representations of HO within 3D images. In certain embodiments, the systems and methods described herein provide a tool that receives a 3D image of a subject and uses a combination of image processing operations to identify regions of the 3D image that correspond to graphical representations of bone, notably including not only normal skeleton, but also HO. In certain embodiments, a final bone mask that identifies normal skeleton and HO regions of a 3D image is determined.

In certain embodiments, once normal skeleton and HO are detected, the systems and methods described herein provide for separation of HO regions from regions corresponding to normal skeleton. In particular, in certain embodiments, the systems and method described herein determine a labeled final bone map that comprises a plurality of discrete and distinguishable labeled regions in an automated fashion. Each labeled region of the final bone map corresponds, in its entirety, to either normal skeleton or HO. Accordingly, in certain embodiments, the systems and methods identify discrete, differentiable regions of a 3D image of subject (e.g., a CT or microCT image) that may then be either manually or automatically classified as either HO or normal skeleton.

Figure 2:
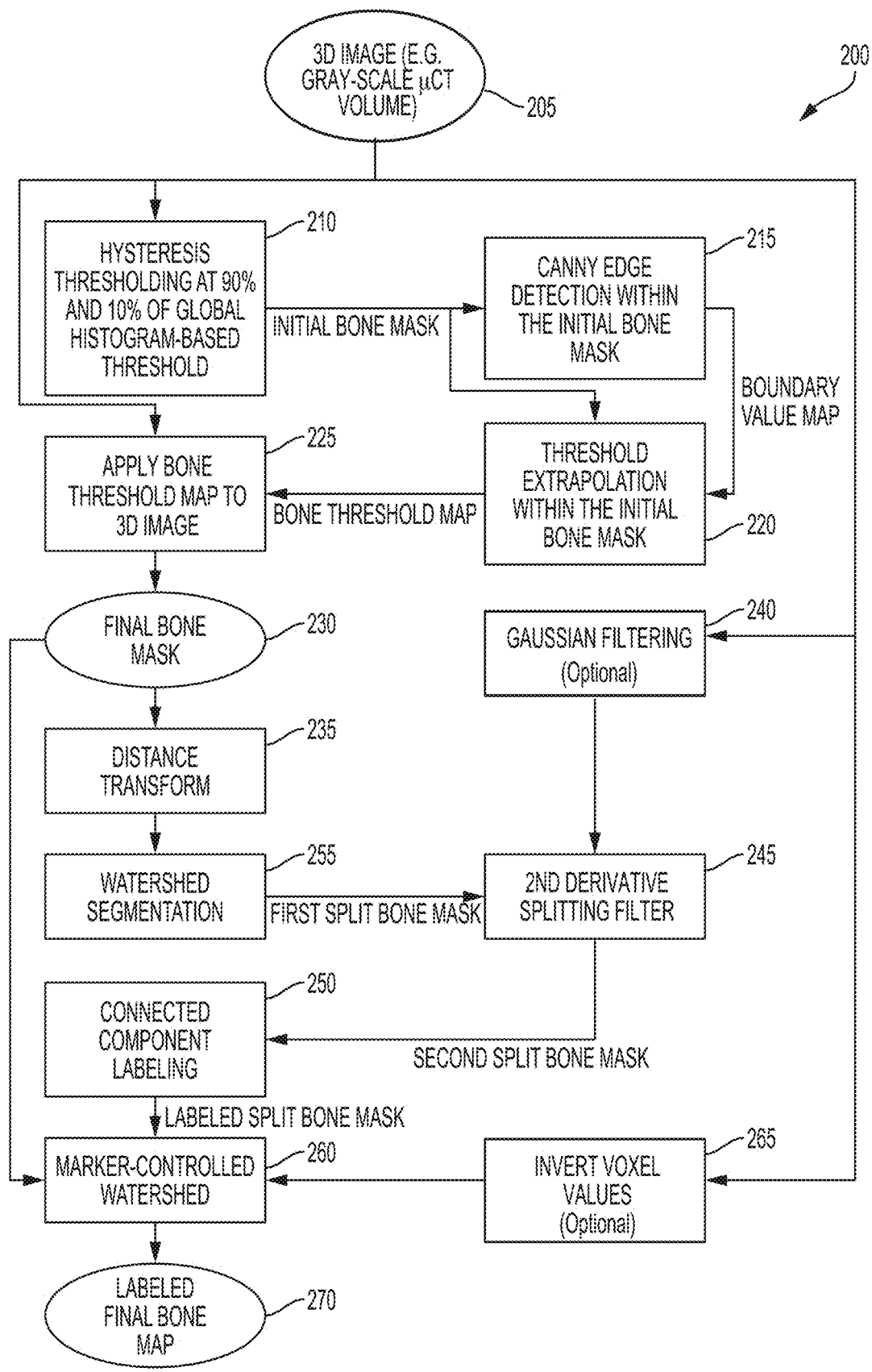
FIG. 2 is a block diagram showing a process for detecting and segmenting normal skeleton and HO, according to an illustrative embodiment.

FIG. 2 shows an example process 200 for detecting and segmenting normal skeleton and HO. The process 200 begins by receiving a 3D image of a subject 205, such as a 3D microCT image. In certain embodiments, the 3D microCT image comprises a plurality of voxels, each of which represents a specific 3D volume within a region of the imaged subject. Each voxel of the 3D image has an intensity value that provides a measure of contrast, as detected via the particular imaging modality used to obtain the 3D image. For example, voxel intensities of 3D microCT images may be represented using Hounsfield unit values, which provide a measure of attenuation that X-rays experience when passing through various regions of the subject before they are detected by an X-ray detector of the microCT detector.

In certain embodiments, the region of the subject that is imaged comprises various structures formed out of bone, including both normal skeleton and HO, along with soft tissue. Accordingly, the received 3D image comprises graphical representations of bone, including normal skeleton and HO, along with soft tissue. An example of a microCT image of hind limbs of a mouse model exhibiting HO is shown in FIG. 1. In the figure, the dark gray regions correspond to graphical representations of bone. Specific regions of HO are indicated, having been identified manually (e.g., via a user manually drawing on the image). Other bone in the image corresponds to normal skeleton.

In certain embodiments, the process 200 comprises two phases. In a first phase, regions of the image corresponding to a graphical representation of bone, including normal skeleton and HO are identified. In certain embodiments, a result of the first phase is a final bone mask 230 that identifies the bone and HO regions of the 3D image. In certain embodiments, in a second phase, the final bone mask is segmented to determine a labeled final bone map 270 that comprises a plurality of discrete and distinguishable labeled regions. The entirety of each labeled region of the labeled final bone map corresponds to either normal skeleton or HO. Accordingly, each labeled region of the final bone map corresponds to either (i) a region of normal skeleton or (ii) a region of HO.

The labeled final bone map determined via the systems and methods described herein facilitates rapid and consistent differentiation between image regions that correspond to either normal skeleton or HO.

A. Detection of Heterotopic Ossification (HO) in a 3D Image

In certain embodiments, detection of HO in a 3D image to determine the final bone mask 230 comprises using a hybrid thresholding approach. The hybrid thresholding approach combines useful features of global and local thresholding techniques to overcome limitations that prevent either technique from accurately and efficiently detecting HO when used in isolation.

In certain embodiments, robust detection of HO is challenging due to structural differences between HO and normal skeleton. For example, HO typically has a more fragmented structure than normal skeleton, which generally corresponds to large, continuous connected regions of bone tissue. As a result, image voxels representing 3D volumes comprising HO generally have lower intensities than image voxels representing 3D volumes comprising normal skeleton.

Such effects are typically referred to as partial volume effects. That is, a given 3D volume corresponding to a region of HO will typically comprise a combination of bone tissue and soft tissue, whereas a 3D volume corresponding to a region of normal skeleton will often comprise almost entirely bone tissue. Image voxels representing HO may, accordingly, have an intensity that is representative of an average (e.g., a volume average) between the amount of bone tissue and soft tissue within the 3D region they represent. Accordingly, differentiating between image voxels that represent regions of HO and image voxels that represent soft tissue is more challenging than differentiating between image voxels representing normal skeleton and image voxels that represent soft tissue.

Global thresholding operations that are often utilized to identify regions of an image that correspond to normal skeleton cannot accurately and robustly identify regions corresponding to HO. Global thresholding operations utilize a single global threshold value across the entire image (e.g., a microCT image) for distinguishing between foreground (e.g., bone) and background (e.g., soft tissue) voxels. The global threshold value is determined based on a distribution of voxel intensities for the entire 3D image (e.g., the distribution being represented via a histogram). An intensity of each voxel within the image is then compared with the global threshold value to identify it as corresponding to foreground (e.g., bone) or background (e.g., soft tissue).

Accordingly, the global threshold value to which a voxel is compared in a global thresholding operation is based on an analysis of the image as whole, and does not account for local variations between different regions of the image. Certain advanced global thresholding techniques, such as hysteresis thresholding, utilize multiple threshold values, but these threshold values are determined as functions of the global threshold value, and, thus, still do not account for local variations between different regions of the image (e.g., threshold values of global thresholding operations are not determined on a voxel-by-voxel basis).

This shortcoming of global thresholding limits its use for accurate and robust detection of HO. For example, one the one hand, a global threshold value that allows for detection of normal skeleton may result in the exclusion of regions of an image that correspond to HO, due to the lower intensity of voxels that correspond to HO regions. On the other hand, a global threshold value that allows all HO regions to be detected may result in over detection of bone regions within an image—that is, various regions of an image corresponding to soft tissue will be incorrectly identified as bone.

Local thresholding approaches employ neighborhood or kernel-based operations to determine specific local threshold values for each voxel of an image, based on an analysis of intensities of neighboring voxels. While local thresholding accounts for local variations between different regions of the image in a manner that global thresholding does not, local thresholding operations are computationally expensive and time consuming due to the fact that they perform a series of neighborhood operations for each voxel in an image (e.g., wherein neighborhood operations determine a threshold value for a given voxel based on intensities of neighboring voxels). The computation cost and time required for a local thresholding operation can be prohibitive for a large 3D image with a large number of voxels. Additionally, local thresholding operations are prone to producing artifacts such as isolated islands incorrectly identified as foreground (e.g., bone).

By combining useful features of global and local thresholding operations, the hybrid thresholding approach utilized by the detection and segmentation tool described herein combines overcomes limitations associated with the individual techniques when used in isolation (e.g., when each approach is used alone), and provides for accurate and robust HO detection in a computationally efficient and rapid fashion.

A.i Global Thresholding and Initial Bone Mask Determination

In certain embodiments, the hybrid thresholding approach applies a global thresholding operation 210 to the 3D image to produce an initial bone mask that identifies an initial region of interest in the 3D image that comprises a graphical representation of bone, including normal skeleton and HO. As described above, global thresholding operations utilize a single global threshold value for distinguishing between foreground (e.g., bone) and background (e.g., soft tissue) voxels.

In certain embodiments, the global threshold value is determined based on a distribution of voxel intensities for the entire 3D image (e.g., the distribution being represented via a histogram). An intensity of each voxel within the image is then compared with the global threshold to identify it as corresponding to foreground (e.g., bone) or background (e.g., soft tissue). For example, a histogram of intensities of voxel of the 3D image can be generated. Often a histogram will show a bi- or multi-modal distribution of voxel intensities (e.g., the histogram will comprise two peaks). Typically a first peak of the distribution primarily comprises intensities of bone voxels, and a second peak of the distribution comprises primarily intensities of voxels corresponding to soft tissue. Accordingly, a global threshold value can be determined as an intensity value falling in between (e.g., in a valley) between the two peaks. A variety of approaches can be used determine global threshold values using the histogram of image voxel intensities, including manual selection (e.g., via a user interaction through a graphical user interface (GUI)) and automated techniques. One example of an automated technique for determining a global threshold value is described in N. Otsu, "A Threshold Selection Method from Gray-Level Histograms, *IEEE Transactions on Systems, Man, and Cybernetics*, vol. 9, no. 1, pgs. 62-66 (1979), the content of which is hereby incorporated by reference in its entirety.

In certain embodiments, global threshold values determined using conventional approaches, when used in a global thresholding operation, result in regions of an image that correspond to HO being incorrectly identified as soft tissue. This may occur, for example, as a result of partial volume effects. Accordingly, in certain embodiments, the global threshold value used in the global thresholding operation 210 is determined such that the global thresholding operation over detects bone tissue. That is, the initial region of interest identified via the initial bone mask includes the entirety of bone tissue regions within the image (e.g., including normal skeleton and HO regions), as well as some regions corresponding to soft tissue. This may be accomplished by, for example, setting the global threshold value lower than would be dictated by conventional analysis of a distribution of voxel intensities of the 3D image. Over detecting bone tissue in this manner ensures that regions of the 3D image corresponding HO are included in the initial region of interest.

In certain embodiments, the global thresholding operation 210 compares, for each voxel of the 3D image, the intensity of the voxel to the determined global threshold value. If the intensity of the voxel of the 3D image is determined to be higher than the global threshold value, then a value of a corresponding voxel in the initial bone mask is assigned a first value that identifies it as corresponding to bone, such as a numeric 1 or a Boolean 'true'. Voxels of the initial bone mask that correspond to image voxels having intensities below the global threshold value are assigned a second value that identifies them as corresponding to soft tissue, such as a numeric 0 or a Boolean 'false'.

In certain embodiments, the global thresholding operation 210 is a hysteresis thresholding operation. The hysteresis thresholding operation uses two thresholds—an upper and lower threshold—that can be determined based on a single global threshold value. For example, upper and lower threshold values may be determined as fractions of the global threshold. For example, the upper threshold may be determined as 90% of the global threshold and the lower threshold determined as 10% of the global threshold value.

In the hysteresis thresholding approach, voxels of the 3D image are first compared to the upper threshold. If a voxel of the 3D image is determined to have an intensity above the upper threshold, it is identified as bone and the value of a corresponding voxel in the initial bone mask is set to a first value, such as a numeric 1 or a Boolean 'false'. Voxels within a specific distance (e.g., a predefined distance) of voxels identified as bone are then searched recursively and compared with the lower threshold. If an intensity value of a voxel within the specific distance of a voxel identified as bone via comparison with the upper threshold is greater than the lower threshold, it is also identified as bone, and a corresponding voxel in the initial bone mask is also assigned the first value. For voxels not identified as bone, corresponding voxels in the initial bone mask are assigned a second value, such as a numeric 0 or Boolean 'false'. In certain embodiments, hysteresis thresholding produces a less "speckled" mask than simpler global thresholding techniques.

Figure 3A:
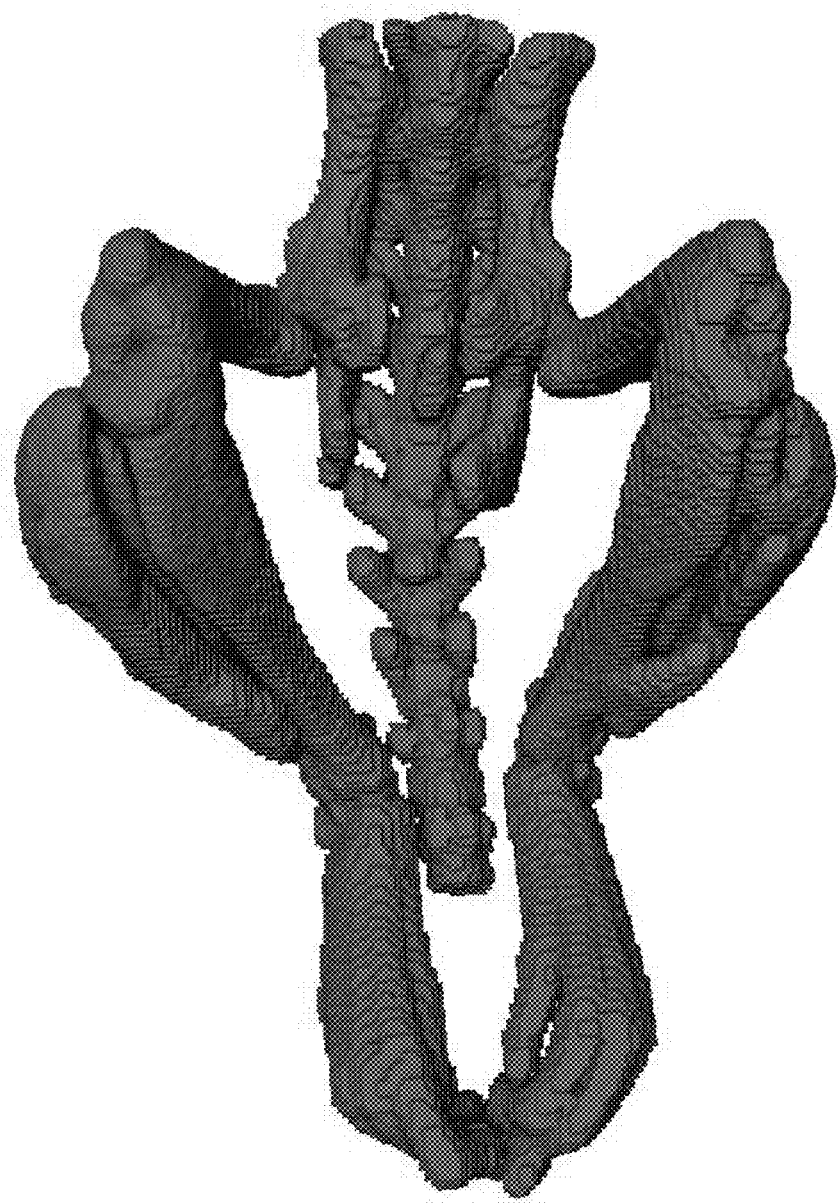
FIG. 3A is an image showing a representation of an initial bone mask determined using the approaches described herein, according to an illustrative embodiment.

FIG. 3A shows an example of an initial bone mask produced from the microCT image shown in FIG. 1. The over representation of bone within the 3D image by the initial bone mask can be observed by comparing the initial bone mask of FIG. 3A with a final bone mask shown in FIG.

3D. The final bone mask shown in FIG. 3D is produced by subsequent steps in the process 200 which refine the initial region of interest using a local thresholding approach.

A.ii Edge Detection and Boundary Value Map Determination

In certain embodiments, once the initial region of interest is established, a local thresholding approach that utilizes a series of operations, including edge detection 215 and threshold extrapolation 220 steps, is applied within the initial region of interest to determine a local threshold value for each voxel within the initial region of interest. Intensities of voxels within the initial region of interest are then compared with their corresponding local threshold values to identify them as foreground (e.g., bone) or background (e.g., soft tissue). In this manner, the initial bone mask that identifies the initial region of interest is refined to produce a final bone mask 230 that accurately identifies regions of the image that correspond to bone tissue, including both normal skeleton and HO.

In certain embodiments, the process 200 includes an edge detection step 215. The edge detection step detects, within the initial region of interest of the 3D image, edge voxels that are one the boundary where bone meets soft tissue. Examples of edge detection methods that may be employed in the edge detection step 215 include, without limitation, Canny edge detection, Sobel edge detection, and methods based on zero-crossing.

Once edge voxels are identified, their intensity values are used to determine a boundary value map. In particular, the boundary value map identifies and includes intensity values of edge voxels of the 3D image (e.g., wherein the edge voxels of the 3D image are voxels that correspond to boundaries where bone meets soft tissue). For example, in certain embodiments, the boundary value map comprises a plurality of voxels, each corresponding to a voxel of the 3D image within the region of interest. Boundary value map voxels that correspond to edge voxels are assigned an intensity value of the corresponding edge voxel of the 3D image and all other boundary value map voxels are assigned a null value (e.g., a numeric 0).

Figure 3B:
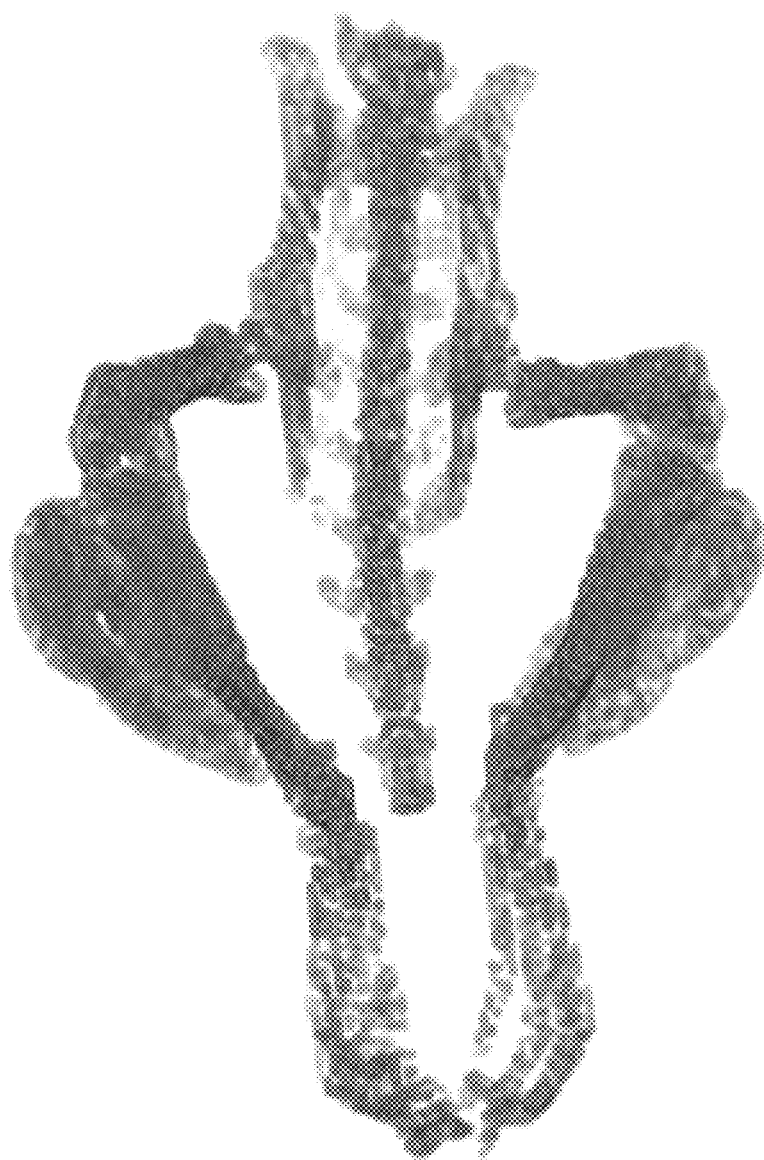
FIG. 3B is an image showing a representation of a boundary value map determined using the approaches described herein, according to an illustrative embodiment.

FIG. 3B shows an example of a boundary value map determined for the initial region of interest identified by the initial bone mask of FIG. 3A. The image of FIG. 3B shows gray scale levels of voxels of the boundary value map shown in FIG. 3B that correspond to edge voxels. Brighter values indicate higher intensities (e.g., larger Hounsfield unit values). Voxels not corresponding to edge voxels are not shown.

A.iii Threshold Extrapolation and Bone Threshold Map Determination

In certain embodiments, in another step in the process 200, the boundary value map is used to determine a bone threshold map for the initial region of interest (e.g., which is identified by the initial bone mask). The bone threshold map comprises a plurality of voxels, each corresponding to a voxel of the 3D image within the initial region of interest identified by the initial bone mask. Each voxel of the bone threshold map has a threshold value that is determined by extrapolating values of the boundary value map to voxels within the initial bone mask. The extrapolation of boundary value map voxels is accomplished in a threshold extrapolation step 220 in which intensity values of the edge voxels included in the boundary value map are progressively extrapolated to neighboring non-edge voxels that correspond to voxels of the 3D image that are within the initial region of interest.

For example, values of the boundary threshold map are initially used as local threshold values for voxels of the bone threshold map that correspond to edge voxels. In a next step a given non-edge voxel of the bone threshold map with several neighboring voxels that correspond to edge voxels is assigned a threshold value determined by averaging the threshold values of the neighboring edge voxels. In subsequent steps, threshold values for voxels of the bone threshold map are determined by averaging values of neighboring voxels for which threshold values have been determined in previous steps, in an iterative fashion, moving inwards within the initial region of interest.

An example approach used in the threshold extrapolation step 220 to determine a bone threshold map is described in detail in J. H. Warsing et al., "An Improved Segmentation Method for In Vivo µCT Imaging," Journal of Bone and Mineral Research, vol. 19, no. 10, pgs. 1640-1650 (2004), the content of which is hereby incorporated by reference in its entirety.

Figure 3C:
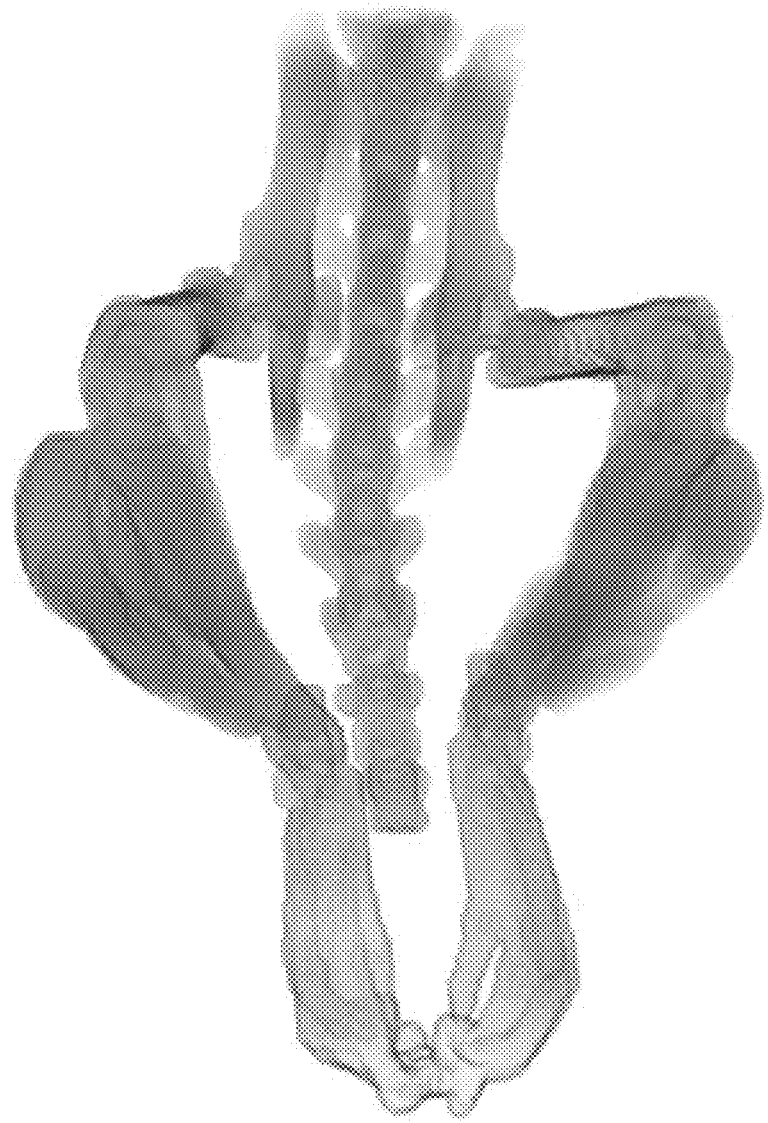
FIG. 3C is an image showing a representation of a bone threshold map determined using the approaches described herein, according to an illustrative embodiment.
Figure 3D:
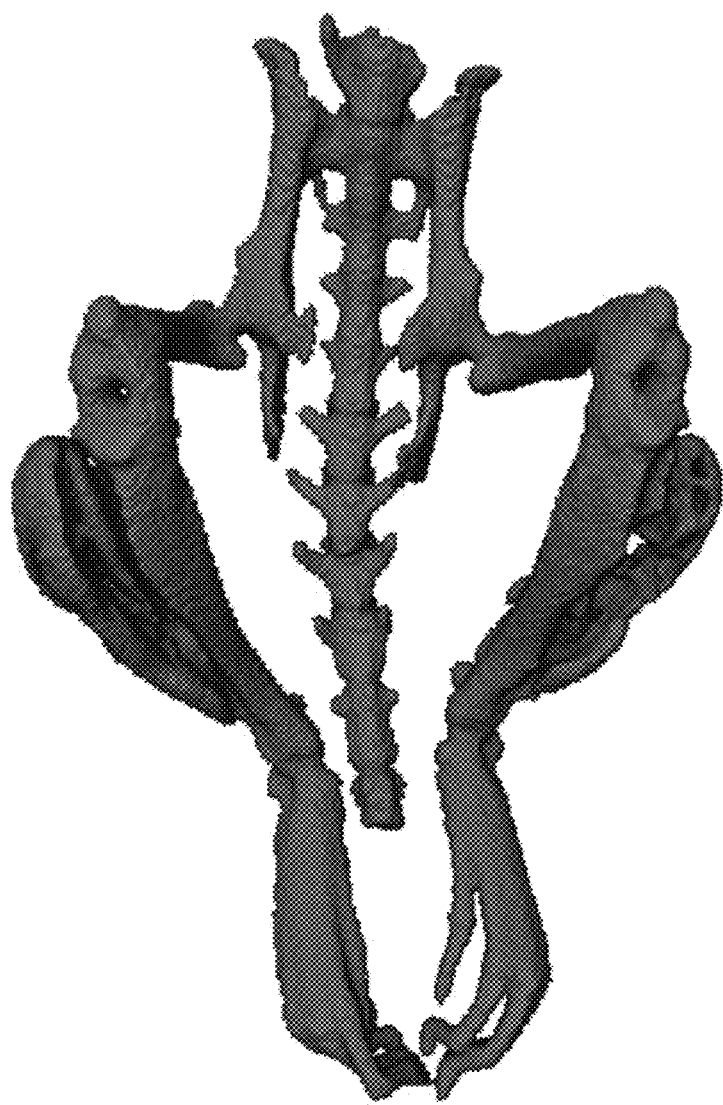
FIG. 3D is an image showing a representation of a final bone mask determined using the approaches described herein, according to an illustrative embodiment.

FIG. 3C shows an example of a bone threshold map determined by threshold extrapolation of the boundary value map of FIG. 3B to the initial region of interest identified by the initial bone mask of FIG. 3A. Brighter gray scale values indicate higher threshold values. Threshold values are not shown for voxels outside of the initial bone mask (hence they make up the white background). Notably, as shown in FIG. 3C the threshold values of the bone threshold map for voxels that lie within several HO regions are lower than those for voxels within normal skeleton regions. Accordingly, the local thresholding approach allows for accurate detection of low-density areas of HO without introducing errors/artifacts in detection of high-density bone or HO components.

A.iv Final Bone Mask Determination

In certain embodiments, the bone threshold map and 3D image are used to determine a final bone mask 230 in a step 225 wherein the bone threshold map is applied to the 3D image. In certain embodiments, the final bone mask 230 is determined by comparing an intensity of each voxel of the 3D image that is within the initial region of interest to the threshold value of a corresponding voxel of the bone threshold map. In certain embodiments, voxels of the 3D image with intensities that are higher than the threshold values of corresponding voxels of the bone threshold map are identified as corresponding to bone (e.g., including normal skeleton and HO), and voxels with intensities that are below the threshold values of corresponding voxels of the bone threshold map are identified as corresponding to non-bone tissue (e.g., soft tissue).

Accordingly, the final bone mask thereby identifies a region of the 3D image that is determined, via the hybrid thresholding approach (e.g., through steps 210, 215, 220, and 225 of the process 200 shown in FIG. 2), to correspond to bone—including normal skeleton and HO. In particular, in certain embodiments, the final bone mask comprises a plurality of voxels, each corresponding to a voxel of the 3D image. Voxels of the final bone mask that correspond to voxels of the 3D image that are identified as corresponding to bone by comparing their intensities with corresponding local threshold values of the bone threshold map are assigned a first value, such as a numeric 1 or Boolean 'true'. All other voxels of the final bone mask are assigned as second value, such as a numeric 0 or Boolean 'false'.

FIG. 3D shows an example of a final bone mask 230 determined via the hybrid thresholding approach described herein. In particular, the final bone mask of FIG. 3D is determined by applying the local thresholding approach comprising steps 215, 220, and 225 of the process 200 shown in FIG. 2 to the initial region of interest identified by the initial bone mask of FIG. 3A. The final bone mask of FIG. 3D identifies a smaller region within the initial region of interest, and excludes regions corresponding to soft tissue that are included in the initial region of interest as a result of over detection by the global thresholding step 210. The final bone map of FIG. 3D thus provides a more accurate identification of regions of the 3D image that correspond to bone (e.g., including normal skeleton and soft tissue) than the initial bone mask.

Notably, by first applying a global thresholding operation 210 to limit the steps directed to determining and applying local threshold values (e.g., edge detection 215, threshold extrapolation 220, and applying the bone threshold map to the 3D image 225) to the initial region of interest, the final bone mask is produced in a computationally efficient fashion. In particular, steps of edge detection 215, threshold extrapolation 220, applying the bone threshold map to the 3D image 225 only need to operate on voxels within the initial region of interest as opposed to the entire image. This reduces computational costs, including processing time, and also eliminates the possibility of any of these steps, or combinations thereof, producing artifacts outside of the initial region of interest. Thus, the hybrid thresholding approach of the systems and methods described herein allows regions of a 3D image to be identified as corresponding to bone tissue, whether normal skeleton or HO, in an accurate, robust, and efficient fashion.

B. Automated Segmentation of Normal Skeleton and Heterotopic Ossification (HO)

In certain embodiments, once normal skeleton and HO are detected, for example via the approaches described above, the systems and methods described herein provide for separation of HO regions from regions corresponding to normal skeleton. Robust separation of HO from normal skeleton is challenging because HO regions often form in close proximity and/or are connected to normal skeleton. For example, the image of FIG. 1 shows HO formed in proximity to the hind limbs of a mouse model. As shown in the figure, the regions of HO are connected to the tibia of the mouse at its ankle joints.

As is evident from FIG. 1, in such situations, differentiating between HO and normal skeleton is non-trivial. Current techniques for image analysis require manual separation of HO from normal skeleton, in which a user is presented with an image and must manually and painstakingly draw boundaries between HO and normal skeleton on the image. Moreover, in addition to being cumbersome, such manual segmentation approaches are prone to human error and inconsistency. Different users may draw different boundaries between HO and normal skeleton, thus the specific regions identified as corresponding to HO via such manual segmentation techniques will vary from user to user. Inconsistencies between boundaries drawn by different users can cause serious and significant errors when, for example, morphometric measurements are determined using HO regions identified in this manner in longitudinal studies.

In certain embodiments, the systems and methods describe herein utilize multiple splitting operations to accurately segment masks that identify regions corresponding to bone. Each of the determined labeled regions corresponds entirely to either bone, or HO. This segmentation is performed automatically, thereby eliminating the need for cumbersome, error prone, and inconsistent manual segmentation based on user interaction.

B.i Distance Transform and Distance Map Determination

In certain embodiments, the approaches described herein comprise using a distance transform in combination with a watershed segmentation operation to produce a first split bone mask. The distance transform and watershed segmentation operations take advantage of the fact that connections between HO and normal skeleton typically take the form of narrow connectors (also referred to as 'necks').

In particular, in certain embodiments, the process 200 comprises a step of applying a distance transform to the final bone mask 235 to determine a distance map. The distance transform determines, for each voxel of the final bone mask corresponding to bone [e.g., assigned the first value (e.g., numeric 1; e.g., Boolean 'false')] a distance from that voxel to a nearest boundary or soft tissue region of the 3D image [e.g., a distance to a nearest voxel of the final bone mask having the second value (e.g., numeric 0; e.g., Boolean 'false')]. The distance transform thus produces a distance map, which comprises a plurality of voxels, each of which corresponds to a voxel of the final bone mask and has (e.g., is assigned) a distance value that represents a distance from the voxel to a nearest boundary and/or non-bone voxel (e.g., a voxel of the final bone mask having a value of 0).

Figure 4:
FIG. 4 is an image showing a representation of a distance map determined using the approaches described herein, according to an illustrative embodiment.

An example distance map determined by applying a distance transform to the final bone mask of FIG. 3D is shown in FIG. 4. Values of the distance map voxels are represented via a green to blue to white color scale, with green representing largest distances, blue representing intermediate distances and white representing 0 distance. That is, voxels that are furthest away from boundaries are colored green, voxels that are an intermediate distance from the boundaries are colored blue, and boundary voxels appear white. Accordingly, the thickest regions of bone are shown in bright green, and the thinnest 'necks' and most fragmented regions of bone in the image are shown as light blue, fading into white.

B.ii Watershed Segmentation and First Split Mask Determination

In certain embodiments, once the distance map is determined, a watershed segmentation step 255 applied to the distance map. The watershed segmentation step 255 includes a watershed segmentation operation that identifies a set of catchment basins and/or watershed lines within the distance map. Catchment basins of the distance map correspond to thicker regions of bone, represented by larger distance values within the distance map. Catchment basins are separated from each other by watershed lines that correspond to connected lines of voxels that correspond to narrow connectors that are often formed between HO and normal skeleton. These narrow connectors are represented by small distance values within the distance map, and, accordingly, identified as watershed lines by the watershed transform.

In certain embodiments, the watershed segmentation operation partitions the distance map into a plurality of catchment basins that are separated from each other by watershed lines. In certain embodiments, the watershed segmentation operation produces a watershed mask comprising a plurality of catchment basins (e.g., each catchment basin corresponding to a connected region of voxels assigned a first value such as a numeric 1 or Boolean 'true') separated from each other by watershed lines (e.g., each watershed line corresponding to a connected line of voxels assigned a second value, such as a numeric 0 or Boolean 'true').

In certain embodiments, a first split bone mask is generated using (A) the final bone mask and (B) the catchment basins and/or watershed lines identified via the watershed segmentation operation. For example, the first split bone mask may be generated by removing voxels corresponding to watershed lines from the final bone mask. In certain embodiments, the first split bone mask is generated by masking the watershed mask with the final bone mask, for example, by performing a logical voxel-by-voxel AND operation between the watershed mask and the final bone mask. In this manner, the distance transform and watershed segmentation steps are used to split the final bone mask, thereby generating the first split bone mask.

Figure 5:
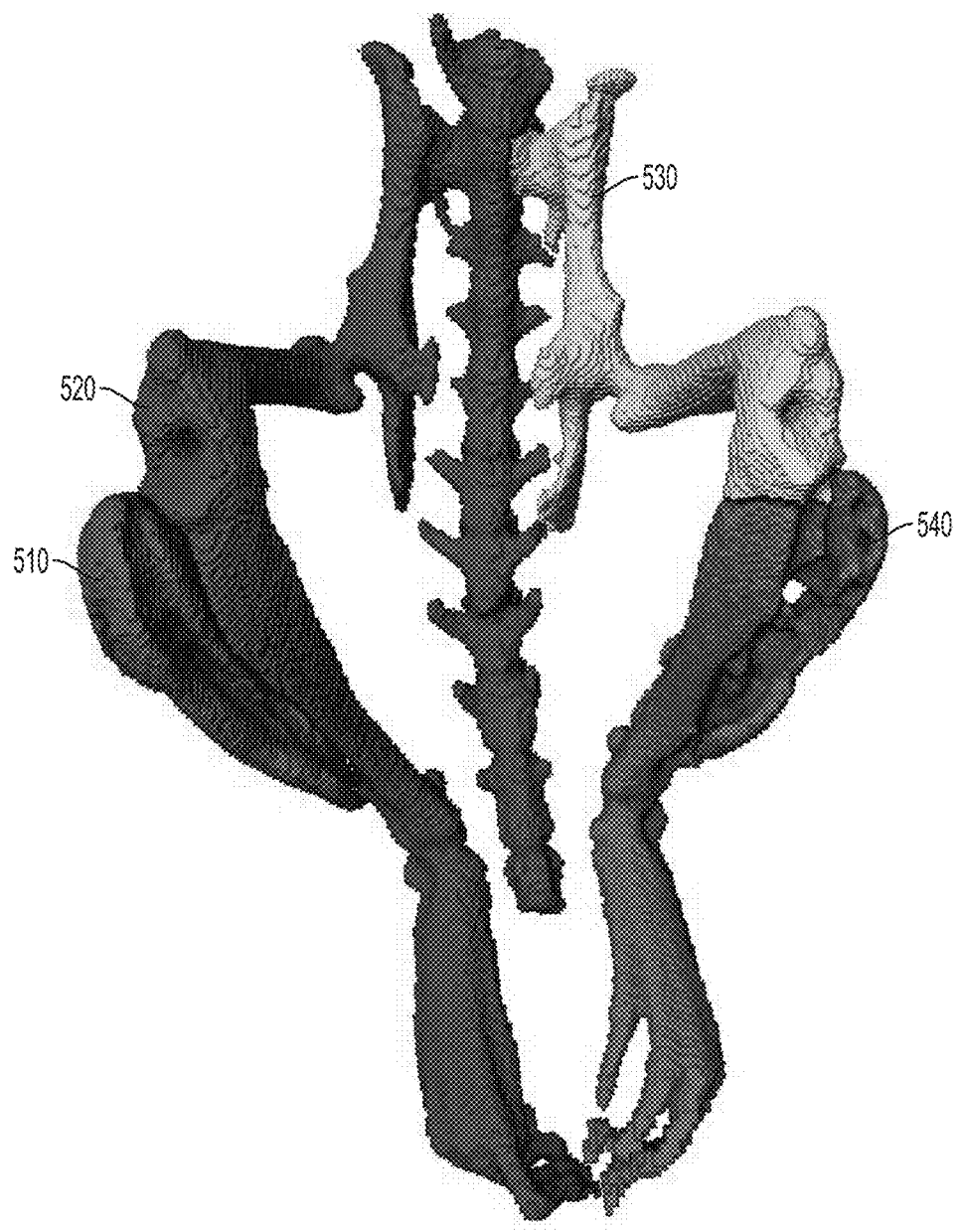
FIG. 5 is an image showing a representation of a first split bone mask determined using the approaches described herein, according to an illustrative embodiment.

FIG. 5 shows an example of a first split bone mask determined via the distance transform 235 and watershed segmentation 255 steps. In certain embodiments, splitting the final bone mask produces a first split bone mask that comprises a plurality of discrete, distinguishable, connected regions. Each region corresponds to a connected set of voxels identified as bone (e.g., assigned the first value, which identifies voxels of the final bone mask as corresponding to bone), separated from other regions by narrow lines of voxels corresponding to split line voxels that were removed from the final bone mask. These distinguishable regions are referred to herein as "split binary components", and can be identified and differentiated from each other via morphological operations such as connected component analysis and labeling. Each identified region can be assigned (e.g., linked to) a distinct label, thereby producing a plurality of labeled split binary components.

For purposes of illustration, the split binary components of the first split bone mask in FIG. 5 have been identified and labeled, and are shown in different colors and identified as regions 510, 520, 530, 540 in the figure. Determination and labeling of split binary components of the first split bone mask is not required, but may be performed in certain embodiments.

B.iii Second Derivative Filtering and Second Split Mask Determination

In certain embodiments, a second splitting step 245 is performed. In certain embodiments, the second splitting step 245 comprises applying one or more second derivative splitting filters to the 3D image. Second derivative splitting filters compute, for a given voxel of a 3D image, a value based on spatial second derivatives, such as a Laplacian value, a highest Hessian eigenvalue, and a lowest Hessian eigenvalue. Voxels of a 3D image to be used as a set of split line voxels are identified by determining values (e.g., a Laplacian; e.g., a highest Hessian eigenvalue; e.g., a lowest Hessian eigenvalue) based on spatial second derivatives of intensity variations across the image, computed at the voxel's position. These values are compared with a threshold value (e.g., a predetermined threshold value) to identify a set of split line voxels. For example, a Laplacian value may be determined for each voxel of the 3D image that corresponds to a voxel within the first split bone mask. In certain embodiments, voxels for which computed Laplacian values are higher than a predetermined threshold value are identified as split line voxels. In certain embodiments, voxels for which computed Laplacian values are lower than a predetermined threshold value are identified as split line voxels. Similar approaches may be used for other values based on spatial second derivatives, such as a highest Hessian eigenvalue, and a lowest Hessian eigenvalue. In certain embodiments, split line voxels determined by one or more second derivative splitting filters are combined within the second set of split line voxels.

In similar fashion to the splitting of the final bone mask via the watershed segmentation step 255, the second splitting step splits the first split bone mask. In particular, in certain embodiments, voxels corresponding to the set of split line voxels identified via second derivative splitting filters are removed from the first split bone mask to produce a second split bone mask. Second derivative splitting filters, their combination, and use in producing split bone masks are described in detail in U.S. application Ser. No. 14/812,483, filed Jul. 29, 2015, the content of which is hereby incorporated by reference in its entirety.

B.iv Connected Component Labeling and Labeled Split Mask Determination

As described above with respect to the first split bone mask, in certain embodiments, the second split bone mask comprises a plurality of split binary components. Split binary components of the second split bone mask correspond to regions produces by removal of voxels corresponding to both the first set of split line voxels and the second set of split line voxels (e.g., by first removing voxels corresponding to the first set of split line voxels from the final bone mask to produce the first split bone mask, followed by removal of voxels corresponding to the second set of split line voxels from the first split bone mask to produce the second split bone mask).

In certain embodiments, a connected component labeling step 250 is performed, wherein morphological operations such as connected component analysis and labeling are used to determine a plurality of such split binary components of the second split bone mask. Each identified region can be assigned (e.g., linked to) a distinct label, thereby producing a plurality of labeled split binary components of the second split bone mask.

Figure 6:
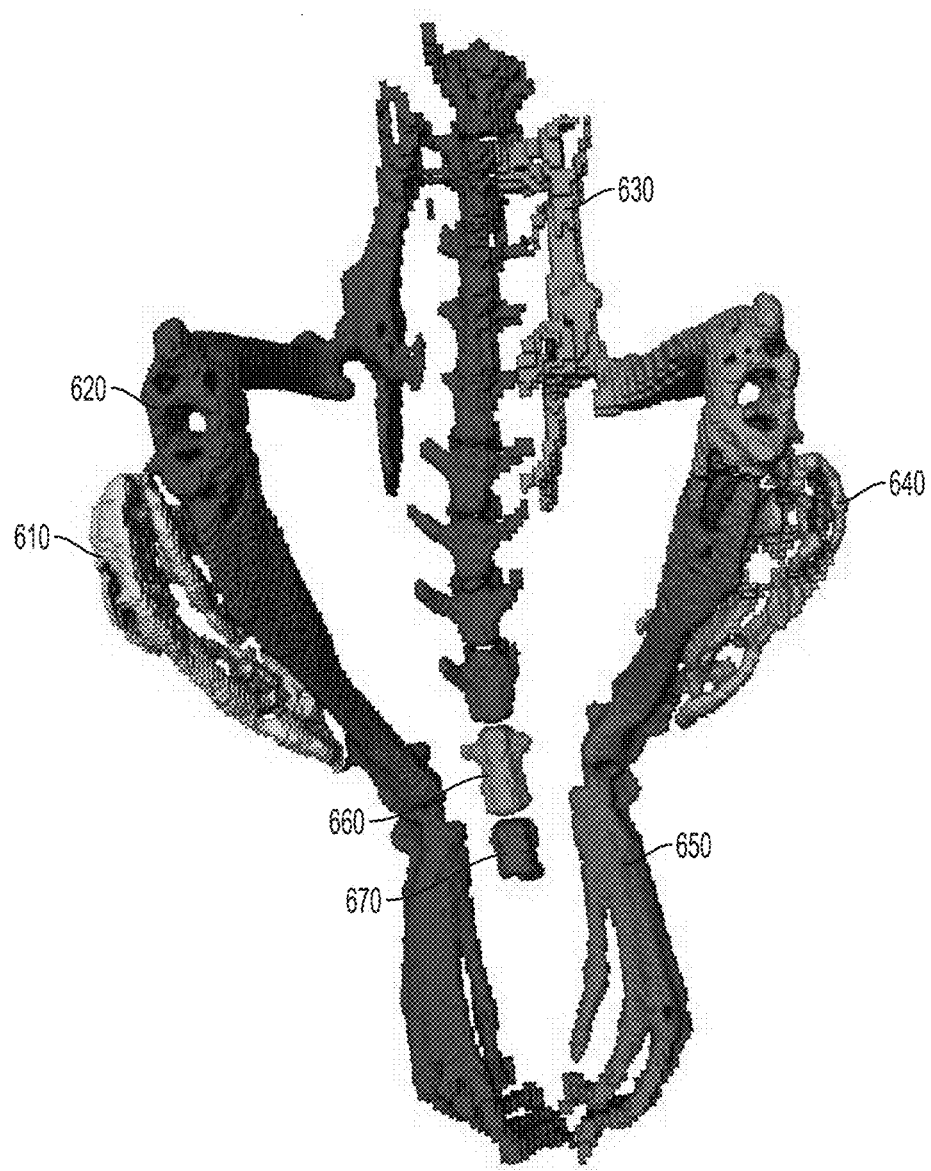
FIG. 6 is an image showing a representation of a plurality of labeled split binary components of a second split bone mask determined using the approaches described herein, according to an illustrative embodiment.

An example of a plurality of labeled split binary components 610, 620, 630, 640, 650, 660, and 670 of the second split bone mask is shown in FIG. 6. The split binary components are shown in different colors.

B.v Marker Controlled Watershed and Labeled Final Bone Map Determination

In certain embodiments, a region growing operation step 260 is performed that uses the plurality of labeled spit binary components of the second split bone mask as seeds, thereby producing a labeled final bone map 270. In certain embodiments, the region growing operation step 260 uses the final bone mask to ensure that the seeds, once expanded via the growing operation are limited to within the final bone mask (e.g., such that the region growing operation is performed within the final bone mask). In certain embodiments, the growing operation step 260 comprises a marker controlled watershed growing operation.

Figure 7:
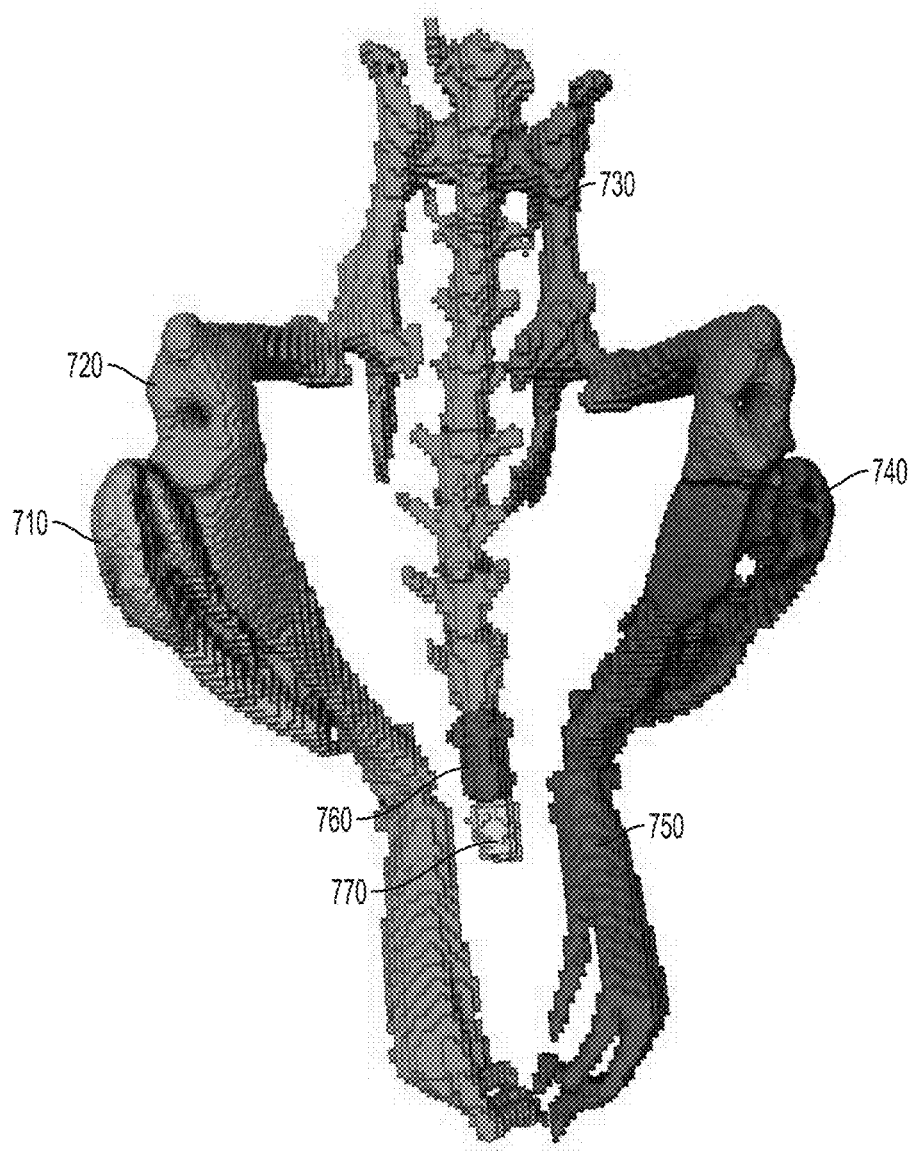
FIG. 7 is an image showing a representation of a labeled final bone map determined using the approaches described herein, according to an illustrative embodiment.

FIG. 7 shows an example of a labeled final bone map produced via a growing step using the labeled split binary components 610, 620, 630, 640, 650, 660, and 670 of the second split bone mask shown in FIG. 6 as seeds. The labeled final bone map that is produced comprises a plurality of labeled regions, the entirety of each region corresponding to either normal skeleton or HO. In FIG. 7, regions 710 and 740 correspond to HO, and regions 720, 730, 750, 760, and 770 correspond to normal skeleton.

B.vi Alternative Embodiments and Optional Steps

Figure 8:
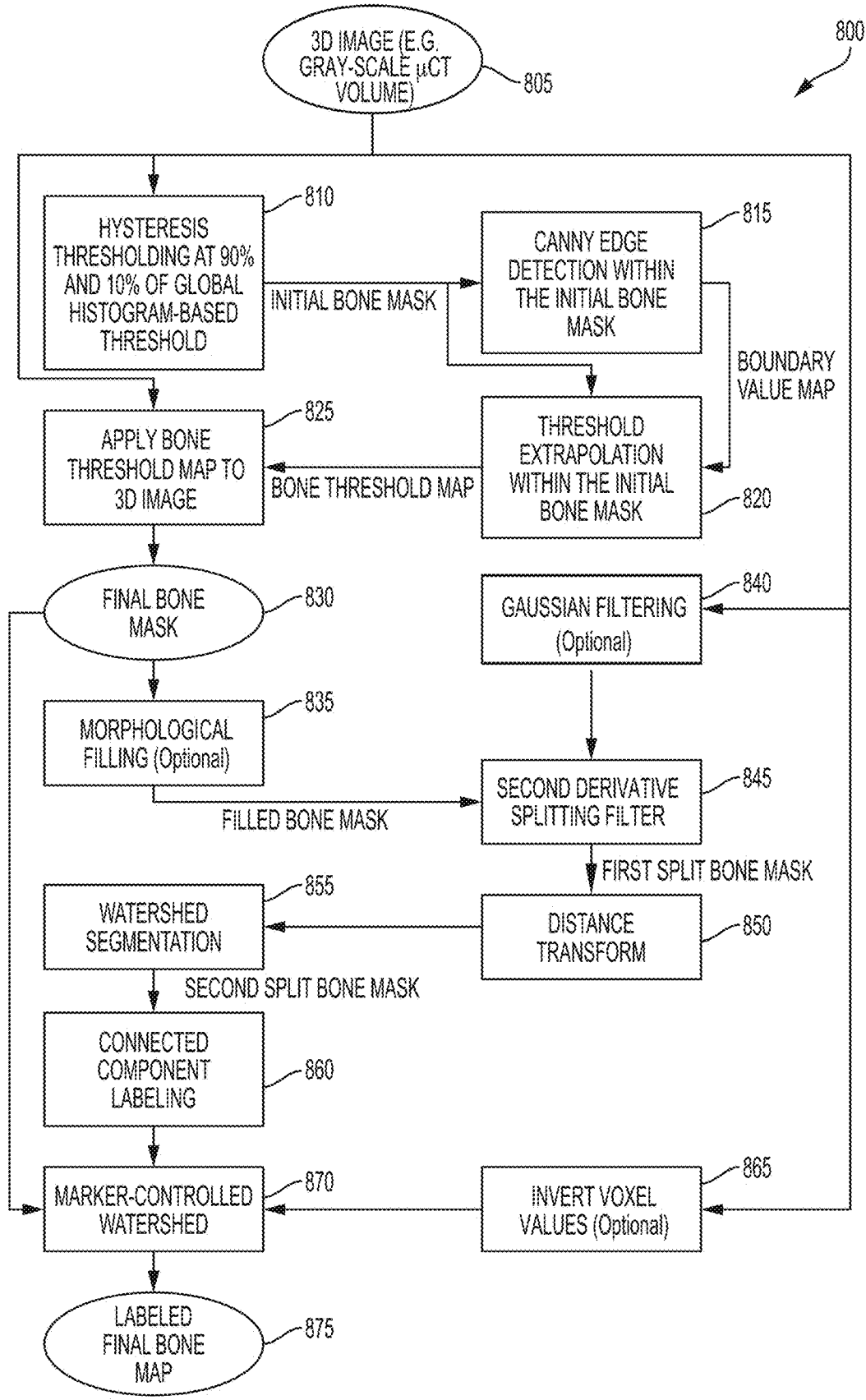
FIG. 8 is a block diagram showing a process for detecting and segmenting normal skeleton and HO, according to an illustrative embodiment.

In certain embodiments, the first split bone mask is produced by first splitting the final bone mask using second derivative filters, after which a distance transform and watershed segmentation step are used to produce a second split bone mask (e.g., step 245 may be performed before steps 235 and 255). FIG. 8 shows an example process 800, similar to process 200, but with the second derivative splitting step 845 performed before the distance transform 850 and watershed segmentation steps 855. In the process 800 shown in FIG. 8, a final bone mask 830 is determined in the same fashion as in the process 200 shown in FIG. 2, via a global thresholding operation 810, edge detection to determine a boundary value map 815, threshold extrapolation 820 to determine a bone threshold map, and determination of the final bone mask 830 by applying 825 the bone threshold map to the 3D image 805.

In certain embodiments, a second derivative filtering step 845 is used to determine a set of split line voxels, and corresponding voxels are removed from the final bone mask to produce a first split bone mask. In certain embodiments, a distance map is determined by applying a distance transform to the first split bone mask 850 after which a watershed segmentation step 855 is applied to the distance map to identify catchment basins and/or watershed lines of the distance map. A second split bone mask is then generated using (A) the first split bone mask and (B) the identified catchment basins and/or watershed lines. As with the example process 200 shown in FIG. 2, a connected component labeling step 860 is used to determine a plurality of split binary components of the second split bone mask, which are then used as seeds in a region growing operation step 870 to produce a labeled final bone map.

Figure 9:
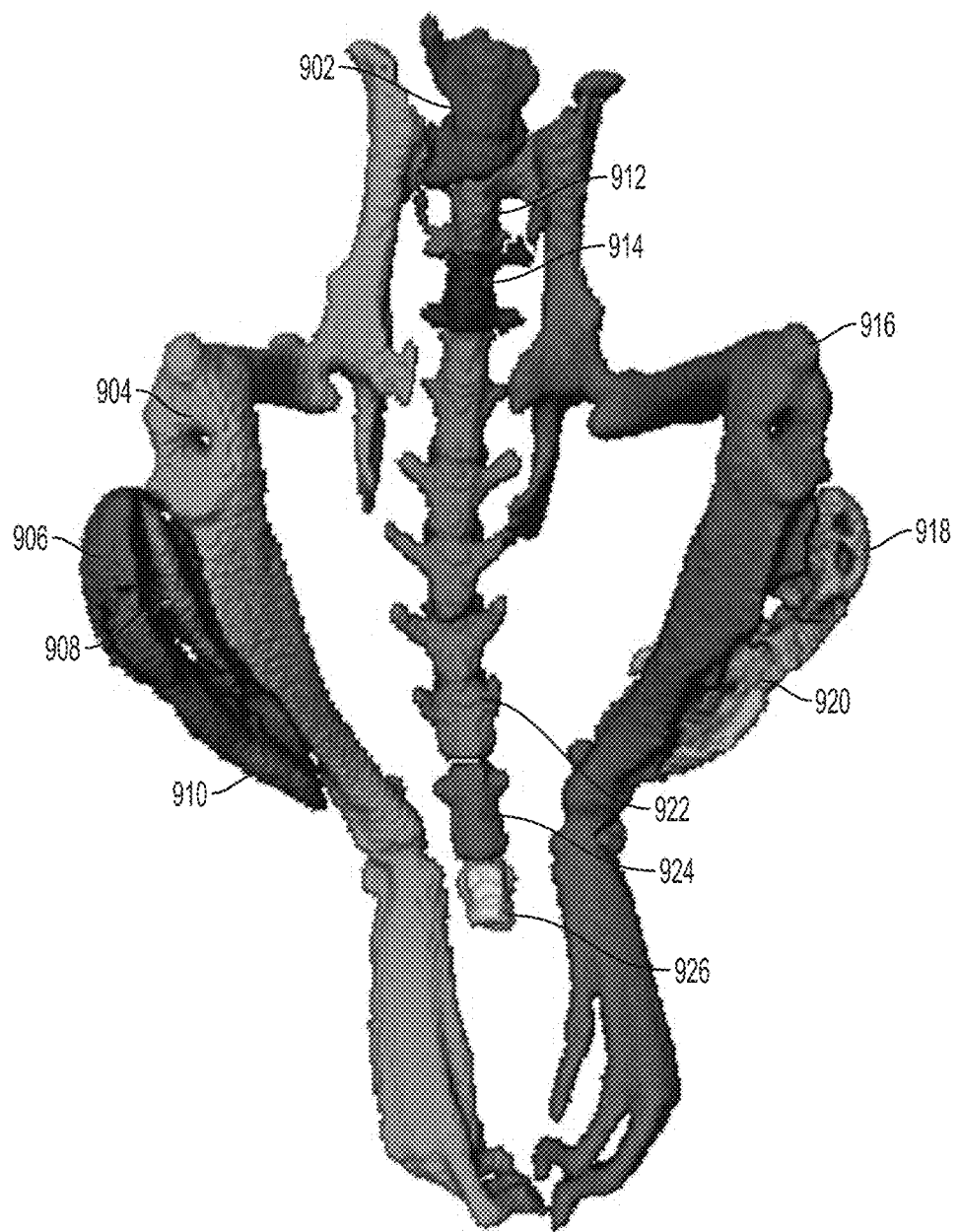
FIG. 9 is an image showing a representation of a labeled final bone map determined using the approaches described herein, according to an illustrative embodiment.

An example of a labeled final bone map 875 produced via process 800 is shown in FIG. 9. In the labeled final bone map of FIG. 9 regions 906, 908, 910, 920, and 918 correspond to HO, and regions 902, 904, 912, 914, 916, 922, 924, and 926 correspond to normal skeleton.

In certain embodiments, additional steps may be included in the HO detection and segmentation approaches described herein. For example, in certain embodiments, an optional morphologic filling step (e.g., 835) is applied after the final bone mask 230, 830 is determined to fill small holes in the final bone mask. In certain embodiments, an optional preliminary Gaussian filtering step 240, 840 is applied to produce a Gaussian filtered version of the 3D image prior to applying the one or more second derivative filters. In certain embodiments, voxel values of the 3D image, and/or any of the masks or maps determined in various steps may be inverted (e.g., via a voxel inversion step 265, 865) by multiplying each voxel intensity by negative one (−1) prior to a given operation, depending on the manner in which the operation is implemented.

C. Additional Processing

C.i User Interaction for Two-Label Map Generation

In certain embodiments, once the labeled final bone map 270 is determined, a graphical representation of the labeled final bone map is presented to a user, who may select labeled regions that correspond to HO and/or normal skeleton. Once the user selects, for example, which labeled regions of the final bone map correspond to HO, the regions are labeled as corresponding to HO and remaining regions are labeled as corresponding to normal skeleton, thereby producing a binary labeled normal skeleton and HO map that differentiates between regions of the 3D image corresponding to normal skeleton and regions of the image corresponding to HO.

In this manner, the systems and methods describe herein accordingly reduce the level of user interaction needed to identify HO regions within an image to simply selecting a given region of a displayed final bone map as corresponding to either HO or normal skeleton. In certain embodiments, this can be accomplished via a few quick 'clicks' (e.g., with a mouse) or 'taps' (e.g., using a touch sensitive interface) within a graphical user interface (GUI). Accordingly, the HO detection and segmentation tool described herein eliminates the cumbersome and laborious process of a user manually drawing boundaries to identify regions of an image that correspond to HO. Moreover, because the plurality of labeled regions of the final bone map are automatically generated, errors and inconsistencies between different users are dramatically reduced (e.g., two or more users are almost guaranteed to select a same set of regions as corresponding to HO, but it is very unlikely for two or more users to draw exactly the same identical boundaries on an image).

C.ii Metric Determination

Accordingly, by providing a tool for automatically detecting and segmenting HO in images of a subject, the systems and methods described herein facilitate the detection and segmentation approaches described herein thereby facilitate streamlined quantitative analysis of HO formation. The systems and methods described herein provide a basis for analysis of morphometric attributes, density, and structural parameters of HO.

For example, once the binary labeled normal skeleton and HO map is determined, it can be used to automatically determine one or more morphometric measurements, relevant for e.g., diagnostics purposes and/or determining treatment efficacy. For example, a total volume of the regions of the binary labeled normal skeleton and HO map that are labeled as corresponding to HO may be computed.

Accordingly, by allowing improved quantitative analysis of HO in this manner, the systems and methods described herein provide a valuable tool for assessing disease state and/or progression in a subject and for assessing treatment efficacy.

C.iii Additional Applications

In certain embodiments, the approaches described herein can be used for detection and segmentation of HO regions in a variety of imaging modalities capable of imaging bone tissue, including microCT, magnetic resonance imaging (MRI), and optical imaging modalities. Additionally, the detection and segmentation approaches described herein can be applied to other image-based object segmentation problems including segmentation of minerals, cells, organs, and other entities in 3D images with low contrast and/or resolution.

D. Computer Systems and Network Environment

Figure 10:
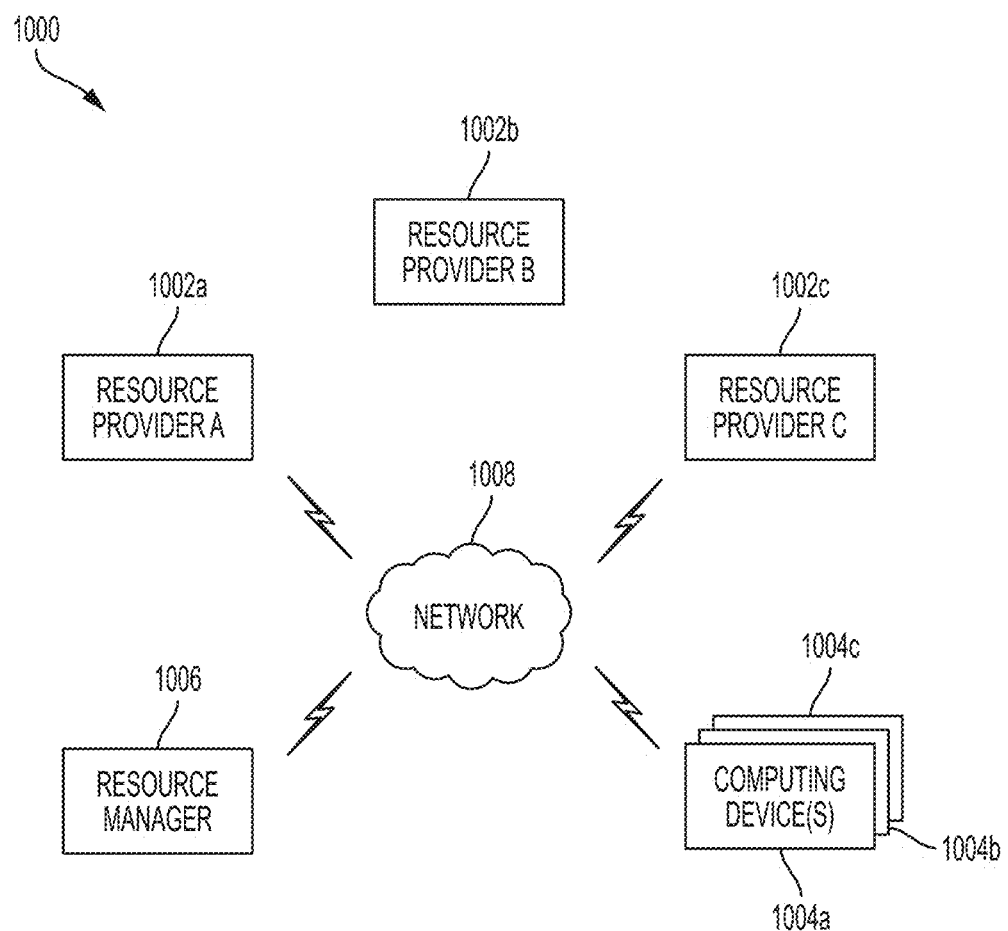
FIG. 10 is a block diagram of an exemplary cloud computing environment, used in certain embodiments.

As shown in FIG. 10, an implementation of a network environment 1000 for use in providing systems and methods for automated detection and segmentation of HO described herein is shown and described. In brief overview, referring now to FIG. 10, a block diagram of an exemplary cloud computing environment 1000 is shown and described. The cloud computing environment 1000 may include one or more resource providers 1002a, 1002b, 1002c (collectively, 1002). Each resource provider 1002 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1002 may be connected to any other resource provider 1002 in the cloud computing environment 1000. In some implementations, the resource providers 1002 may be connected over a computer network 1008. Each resource provider 1002 may be connected to one or more computing device 1004a, 1004b, 1004c (collectively, 1004), over the computer network 1008.

The cloud computing environment 1000 may include a resource manager 1006. The resource manager 1006 may be connected to the resource providers 1002 and the computing devices 1004 over the computer network 1008. In some implementations, the resource manager 1006 may facilitate the provision of computing resources by one or more resource providers 1002 to one or more computing devices 1004. The resource manager 1006 may receive a request for a computing resource from a particular computing device 1004. The resource manager 1006 may identify one or more resource providers 1002 capable of providing the computing resource requested by the computing device 1004. The resource manager 1006 may select a resource provider 1002 to provide the computing resource. The resource manager 1006 may facilitate a connection between the resource provider 1002 and a particular computing device 1004. In some implementations, the resource manager 1006 may establish a connection between a particular resource provider 1002 and a particular computing device 1004. In some implementations, the resource manager 1006 may redirect a particular computing device 1004 to a particular resource provider 1002 with the requested computing resource.

Figure 11:
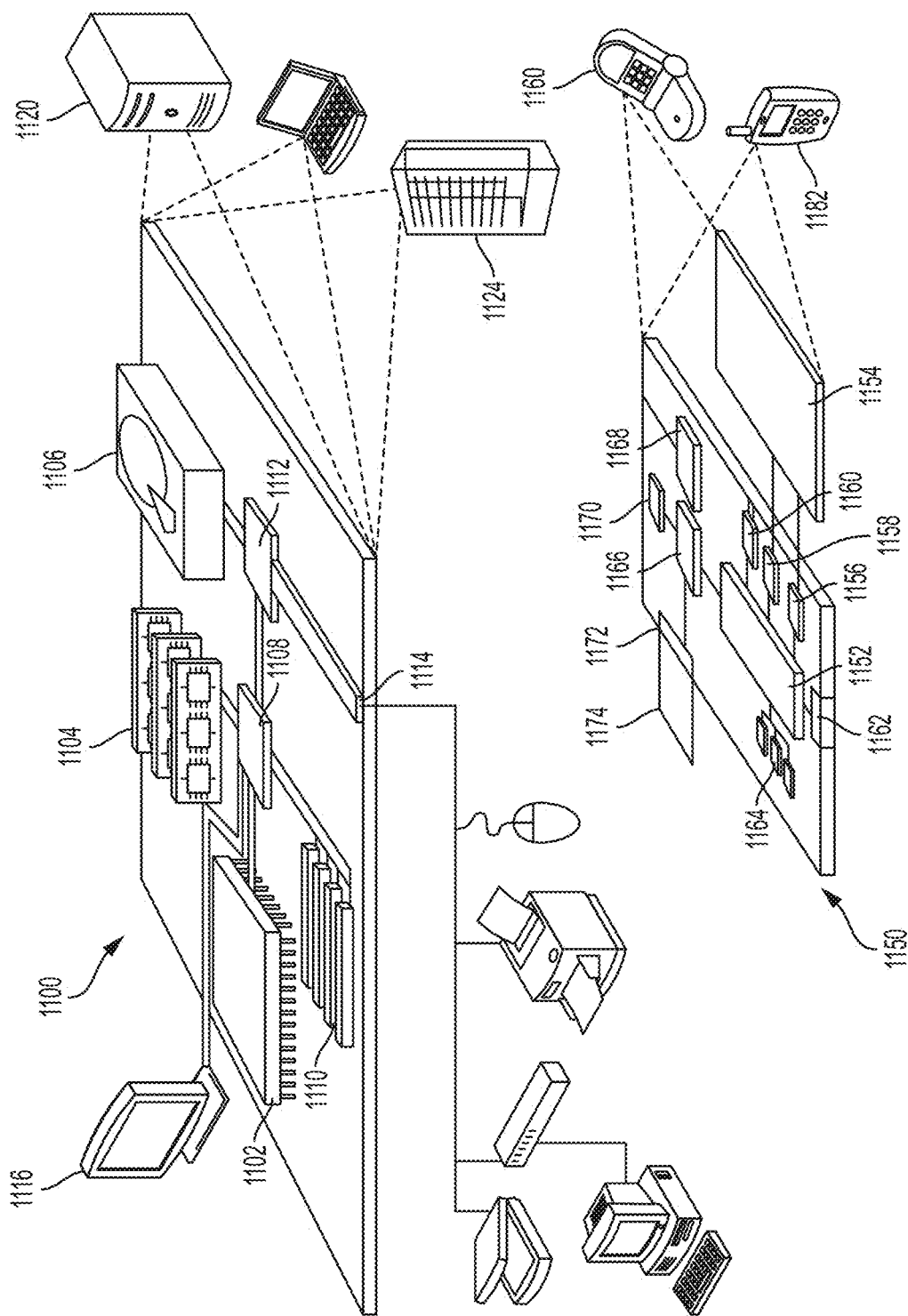
FIG. 11 is a block diagram of an example computing device and an example mobile computing device used in certain embodiments.

FIG. 11 shows an example of a computing device 1100 and a mobile computing device 1150 that can be used to implement the techniques described in this disclosure. The computing device 1100 is intended to represent various forms of digital computers, such as laptops, desktops, workstations, personal digital assistants, servers, blade servers, mainframes, and other appropriate computers. The mobile computing device 1150 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1104 stores information within the computing device 1100. In some implementations, the memory 1104 is a volatile memory unit or units. In some implementations, the memory 1104 is a non-volatile memory unit or units. The memory 1104 may also be another form of computer-readable medium, such as a magnetic or optical disk.

The storage device 1106 is capable of providing mass storage for the computing device 1100. In some implementations, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1102), perform one or more methods, such as those described above. The instructions can also be stored by one or more storage devices such as computer- or machine-readable mediums (for example, the memory 1104, the storage device 1106, or memory on the processor 1102).

The high-speed interface 1108 manages bandwidth-intensive operations for the computing device 1100, while the low-speed interface 1112 manages lower bandwidth-intensive operations. Such allocation of functions is an example only. In some implementations, the high-speed interface 1108 is coupled to the memory 1104, the display 1116 (e.g., through a graphics processor or accelerator), and to the high-speed expansion ports 1110, which may accept various expansion cards (not shown). In the implementation, the low-speed interface 1112 is coupled to the storage device 1106 and the low-speed expansion port 1114. The low-speed expansion port 1114, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. In addition, it may be implemented in a personal computer such as a laptop computer 1122. It may also be implemented as part of a rack server system 1124. Alternatively, components from the computing device 1100 may be combined with other components in a mobile device (not shown), such as a mobile computing device 1150. Each of such devices may contain one or more of the computing device 1100 and the mobile computing device 1150, and an entire system may be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 may also be provided with a storage device, such as a micro-drive or other device, to provide additional storage. Each of the processor 1152, the memory 1164, the display 1154, the communication interface 1166, and the transceiver 1168, are interconnected using various buses, and several of the components may be mounted on a common motherboard or in other manners as appropriate.

The processor 1152 can execute instructions within the mobile computing device 1150, including instructions stored in the memory 1164. The processor 1152 may be implemented as a chipset of chips that include separate and multiple analog and digital processors. The processor 1152 may provide, for example, for coordination of the other components of the mobile computing device 1150, such as control of user interfaces, applications run by the mobile computing device 1150, and wireless communication by the mobile computing device 1150.

The processor 1152 may communicate with a user through a control interface 1158 and a display interface 1156 coupled to the display 1154. The display 1154 may be, for example, a TFT (Thin-Film-Transistor Liquid Crystal Display) display or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may provide communication with the processor 1152, so as to enable near area communication of the mobile computing device 1150 with other devices. The external interface 1162 may provide, for example, for wired communication in some implementations, or for wireless communication in other implementations, and multiple interfaces may also be used.

The memory 1164 stores information within the mobile computing device 1150. The memory 1164 can be implemented as one or more of a computer-readable medium or media, a volatile memory unit or units, or a non-volatile memory unit or units. An expansion memory 1174 may also be provided and connected to the mobile computing device 1150 through an expansion interface 1172, which may include, for example, a SIMM (Single In Line Memory Module) card interface. The expansion memory 1174 may provide extra storage space for the mobile computing device 1150, or may also store applications or other information for the mobile computing device 1150. Specifically, the expansion memory 1174 may include instructions to carry out or supplement the processes described above, and may include secure information also. Thus, for example, the expansion memory 1174 may be provide as a security module for the mobile computing device 1150, and may be programmed with instructions that permit secure use of the mobile computing device 1150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. That the instructions, when executed by one or more processing devices (for example, processor 1152), perform one or more methods, such as those described above. The instructions can also be stored by one or more storage devices, such as one or more computer- or machine-readable mediums (for example, the memory 1164, the expansion memory 1174, or memory on the processor 1152). In some implementations, the instructions can be received in a propagated signal, for example, over the transceiver 1168 or the external interface 1162.

The mobile computing device 1150 may communicate wirelessly through the communication interface 1166, which may include digital signal processing circuitry where necessary. The communication interface 1166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1168 using a radio-frequency. In addition, short-range communication may occur, such as using a Bluetooth®, Wi-Fi™, or other such transceiver (not shown). In addition, a GPS (Global Positioning System) receiver module 1170 may provide additional navigation- and location-related wireless data to the mobile computing device 1150, which may be used as appropriate by applications running on the mobile computing device 1150.

The mobile computing device 1150 may also communicate audibly using an audio codec 1160, which may receive spoken information from a user and convert it to usable digital information. The audio codec 1160 may likewise generate audible sound for a user, such as through a speaker, e.g., in a handset of the mobile computing device 1150. Such sound may include sound from voice telephone calls, may include recorded sound (e.g., voice messages, music files, etc.) and may also include sound generated by applications operating on the mobile computing device 1150.

The mobile computing device 1150 may be implemented in a number of different forms, as shown in the figure. For example, it may be implemented as a cellular telephone 1180. It may also be implemented as part of a smart-phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, any modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically detecting heterotopic ossification (HO) in a 3D image of a subject, the method comprising:
   (a) receiving, by a processor of a computing device, the 3D image of a subject;
   (b) applying, by the processor, a global thresholding operation to the 3D image to produce an initial bone mask that identifies an initial region of interest within the image comprising a graphical representation of bone;
   (c) determining, by the processor, a boundary value map using a 3D edge detection operation applied to the initial region of interest of the 3D image identified by the initial bone mask, wherein the boundary value map identifies and includes intensity values of voxels of the 3D image that correspond to boundaries where bone meets soft tissue;
   (d) determining, by the processor, a bone threshold map using the initial bone mask and the boundary value map, wherein the bone threshold map comprises, for each voxel of the initial bone mask, a threshold value determined by extrapolating values of the boundary value map to voxels within the initial bone mask;
   (e) determining, by the processor, a final bone mask using the bone threshold map and the 3D image;
   (f) determining, by the processor, a distance map by applying a distance transform to the final bone mask;
   (g) applying, by the processor, a watershed segmentation operation to the distance map to identify at least one of a set of catchment basins and watershed lines within the distance map;
   (h) generating, by the processor, a first split bone mask using the final bone mask and at least one of the identified catchment basins and the watershed lines from act (g);
   (i) applying, by the processor, one or more second derivative splitting filters to the 3D image to identify a set of split line voxels within the 3D image;
   (j) removing, by the processor, voxels corresponding to the set of split line voxels from the first split bone mask, thereby generating a second split bone mask;
   (k) determining, by the processor, a plurality of labeled split binary components of the second split bone mask via one or more morphological processing operations;
   (l) performing, by the processor, a region growing operation within the final bone mask using the plurality of labeled split binary components of the second split bone mask as seeds, thereby producing a labeled final bone map; and
   (m) rendering, by the processor, a graphical representation of the labeled final bone map.

2. The method of claim 1, wherein act (b) comprises determining, by the processor, a global threshold value using intensities of voxels of the 3D image.

3. The method of claim 2, wherein the global threshold value is determined such that the initial bone mask that over represents bone within the 3D image.

4. The method of claim 2, wherein the global thresholding operation is a hysteresis thresholding operation that uses an upper threshold and a lower threshold determined using the global threshold value.

5. The method of claim 1, comprising:
   (n) following act (m), receiving, by the processor, via a graphical user interface (GUI), a user selection of one or more of a plurality of labeled regions of the labeled final bone map, wherein the user selection corresponds to an identification of the one or more labeled regions as corresponding to HO; and
   (o) labeling, by the processor, the one or more labeled regions selected by the user as corresponding to HO and labeling, by the processor, the remaining labeled regions of the plurality of labeled regions as corresponding to normal skeleton, thereby producing a binary labeled normal skeleton and HO map that differentiates between regions of the 3D image corresponding to normal skeleton and regions of the image corresponding to HO.

6. The method of claim 5, comprising determining, by the processor, one or more morphometric measurements using the binary labeled normal skeleton and HO map.

7. The method of claim 6, comprising determining, by the processor, a total volume of the regions of the binary labeled normal skeleton and HO map that are labeled as corresponding to HO.

8. The method of claim 1, wherein the one or more second derivative splitting filters comprises at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

9. The method of claim 1, wherein applying the one or more second derivative splitting filters comprises applying a plurality of second derivative splitting filters, wherein applying the plurality of second derivative splitting filters comprises:
for each second derivative splitting filter being applied, producing a filtered image and identifying voxels of the filtered image with intensity higher or lower than a threshold value as split line voxels.

10. The method of claim 1, comprising:
prior to applying the one or more second derivative splitting filters, performing, by the processor, a Gaussian filtering operation on the 3D image to produce a Gaussian filtered version of the 3D image; and
applying, by the processor, the one or more second derivative splitting filters to the Gaussian filtered version of the 3D image.

11. The method of claim 1, wherein the 3D image of the subject is a CT image and wherein the method comprises acquiring the CT image.

12. A method for automatically detecting heterotopic ossification (HO) in a 3D image of a subject, the method comprising:
(a) receiving, by a processor of a computing device, the 3D image of a subject;
(b) applying, by the processor, a global thresholding operation to the received 3D image to produce an initial bone mask that identifies an initial region of interest within the 3D image comprising a graphical representation of bone;
(c) determining, by the processor, a boundary value map using a 3D edge detection operation applied to the initial region of interest of the 3D image identified by the initial bone mask, wherein the boundary value map identifies and includes intensity values of voxels of the 3D image that correspond to boundaries where bone meets soft tissue;
(d) determining, by the processor, a bone threshold map using the initial bone mask and the boundary value map, wherein the bone threshold map comprises, for each voxel of the initial bone mask, a threshold value determined by extrapolating values of the boundary value map to voxels within the initial bone mask;
(e) determining, by the processor, a final bone mask using the bone threshold map and the 3D image;
(f) applying, by the processor, one or more second derivative splitting filters to the 3D image to identify a set of split line voxels within the 3D image;
(g) removing, by the processor, voxels corresponding to the set of split line voxels from the final bone mask, thereby generating a first split bone mask;

(h) determining, by the processor, a distance map by applying a distance transform to the first split bone mask;
(i) applying, by the processor, a watershed segmentation operation to the distance map to identify at least one of a set of catchment basins and watershed lines within the distance map;
(j) generating, by the processor, a second split bone mask using (A) the first split bone mask and (B) at least one of the identified catchment basins and watershed lines from act (i);
(k) determining, by the processor, a plurality of labeled split binary components of the second split bone mask via one or more morphological processing operations;
(l) performing, by the processor, a region growing operation within the final bone mask using the plurality of labeled spit binary components of the second split bone mask as seeds, thereby producing a labeled final bone map; and
(m) rendering, by the processor, a graphical representation of the labeled final bone map.

13. A system for automated detection of heterotopic ossification (HO) in a 3D image of a subject, the system comprising:
a processor; and
a memory having instructions stored thereon, wherein the instructions, when executed by the processor, cause the processor to:
(a) receive the 3D image of the subject;
(b) apply a global thresholding operation to the received 3D image to produce an initial bone mask that identifies an initial region of interest within the 3D image comprising a graphical representation of bone;
(c) determine a boundary value map using a 3D edge detection operation applied to the initial region of interest of the 3D image identified by the initial bone mask, wherein the boundary value map identifies and includes intensity values of voxels of the 3D image that correspond to boundaries where bone meets soft tissue;
(d) determine a bone threshold map using the initial bone mask and the boundary value map, wherein the bone threshold map comprises, for each voxel of the initial bone mask, a threshold value determined by extrapolating values of the boundary value map to voxels within the initial bone mask;
(e) determine a final bone mask using the bone threshold map and the 3D image;
(f) determine a distance map by applying a distance transform to the final bone mask;
(g) apply a watershed segmentation operation to the distance map to identify at least one of a set of catchment basins and watershed lines within the distance map;
(h) generate a first split bone mask using the final bone mask and at least one of the identified catchment basins and the watershed lines from act (g);
(i) apply one or more second derivative splitting filters to the 3D image to identify a set of split line voxels within the 3D image;
(j) remove voxels corresponding to the set of split line voxels from the first split bone mask, thereby generating a second split bone mask;
(k) determine a plurality of labeled split binary components of the second split bone mask via one or more morphological processing operations;
(l) perform a region growing operation within the final bone mask using the plurality of labeled split binary components of the second split bone mask as seeds, thereby producing a labeled final bone map; and (m) render a graphical representation of the labeled final bone map.

14. The system of claim 13, wherein, at act (b), the instructions cause the processor to determine a global threshold value using intensities of voxels of the 3D image.

15. The system of claim 14, wherein the instructions cause the processor to determine the global threshold such that the initial bone mask that over represents bone within the 3D image.

16. The system of claim 14, wherein the global thresholding operation is a hysteresis thresholding operation that uses an upper threshold and a lower threshold determined using the global threshold value.

17. The system of claim 13, wherein the instructions cause the processor to:

(n) following act (m), receive, via a graphical user interface (GUI), a user selection of one or more of a plurality of labeled regions of the labeled final bone map, wherein the user selection corresponds to an identification of the one or more labeled regions as corresponding to HO; and (o) label the one or more labeled regions selected by the user as corresponding to HO and label the remaining labeled regions of the plurality of labeled regions as corresponding to normal skeleton, thereby producing a binary labeled normal skeleton and HO map that differentiates between regions of the 3D image corresponding to normal skeleton and regions of the image corresponding to HO.

18. The system of claim 17, wherein the instructions cause the processor to determine one or more morphometric measurements using the binary labeled normal skeleton and HO map.

19. The system of claim 18, wherein the instructions cause the processor to determine a total volume of the regions of the binary labeled normal skeleton and HO map that are labeled as corresponding to HO.

20. The system of claim 13, wherein the one or more second derivative splitting filters comprises at least one member selected from the group consisting of a LoG (Laplacian of Gaussian), a HEH (highest Hessian eigenvalue, with preliminary Gaussian filtering), and a LEH (lowest Hessian eigenvalue, with preliminary Gaussian filtering).

21. The system of claim 13, wherein applying the one or more second derivative splitting filters comprises applying a plurality of second derivative splitting filters, wherein applying the plurality of second derivative splitting filters comprises:

for each second derivative splitting filter being applied, producing a filtered image and identifying voxels of the filtered image with intensity higher or lower than a threshold value as split line voxels.

22. The system of claim 13, wherein the instructions cause the processor to:

prior to applying the one or more second derivative splitting filters, perform a Gaussian filtering operation on the 3D image to produce a Gaussian filtered version of the 3D image; and apply the one or more second derivative splitting filters to the Gaussian filtered version of the 3D image.

23. The system of claim 13, wherein the 3D image of the subject is a CT image.

24. The system of claim 23, wherein the system comprises a CT scanner for acquiring the 3D image of the subject and wherein the instructions cause the processor to acquire the 3D image of the subject using the CT scanner.

25. A system for automated detection of heterotopic ossification (HO) in a 3D image of a subject, the system comprising:

a processor; and a memory having instructions stored thereon, wherein the instructions, when executed by the processor, cause the processor to:

(a) receive the 3D image of the subject;

(b) apply a global thresholding operation to the received 3D image to produce an initial bone mask that identifies an initial region of interest within the image comprising a graphical representation of bone;

(c) determine a boundary value map using a 3D edge detection operation applied to the initial region of interest of the 3D image identified by the initial bone mask, wherein the boundary value map identifies and includes intensity values of voxels of the 3D image that correspond to boundaries where bone meets soft tissue;

(d) determine a bone threshold map using the initial bone mask and the boundary value map, wherein the bone threshold map comprises, for each voxel of the initial bone mask, a threshold value determined by extrapolating values of the boundary value map to voxels within the initial bone mask;

(e) determine a final bone mask using the bone threshold map and the 3D image;

(f) apply one or more second derivative splitting filters to the 3D image to identify a set of split line voxels within the 3D image;

(g) remove voxels corresponding to the set of split line voxels from the final bone mask, thereby generating a first split bone mask;

(h) determine a distance map by applying a distance transform to the first split bone mask; and (i) apply a watershed segmentation operation to the distance map to identify at least one of a set of catchment basins and watershed lines within the distance map;

(j) generate a second split bone mask using (A) the first split bone mask and (B) at least one of the identified catchment basins and watershed lines from act (i);

(k) determine a plurality of labeled split binary components of the second split bone mask via one or more morphological processing operations;

(l) perform a region growing operation within the final bone mask using the plurality of labeled spit binary components of the second split bone mask as seeds, thereby producing a labeled final bone map; and (m) render a graphical representation of the labeled final bone map.

* * * * *